United States Patent
Seong et al.

(10) Patent No.: US 11,248,023 B2
(45) Date of Patent: *Feb. 15, 2022

(54) AGONIST OF SPEXIN-BASED GALANIN TYPE 2 RECEPTOR AND USE THEREOF

(71) Applicant: NEURACLE SCIENCE CO., LTD., Seoul (KR)

(72) Inventors: Jae Young Seong, Seoul (KR); Jong-Ik Hwang, Seoul (KR); Dong-Hoon Kim, Seoul (KR); Gi Hoon Son, Seoul (KR); Yoo-Na Lee, Seoul (KR); Seongsik Yun, Daejeon (KR); Arfaxad Reyes-Alcaraz, Seoul (KR)

(73) Assignee: Neuracle Science Co., Ltd, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/511,976

(22) Filed: Jul. 15, 2019

(65) Prior Publication Data

US 2020/0010509 A1 Jan. 9, 2020

Related U.S. Application Data

(63) Continuation of application No. 15/771,078, filed as application No. PCT/KR2016/013950 on Nov. 30, 2016, now Pat. No. 10,385,098.

(30) Foreign Application Priority Data

Nov. 30, 2015 (KR) .......................... 10-2015-0168555

(51) Int. Cl.
| | |
|---|---|
| *C07K 7/08* | (2006.01) |
| *A61K 38/00* | (2006.01) |
| *A61P 25/28* | (2006.01) |
| *A61P 25/30* | (2006.01) |
| *A61P 25/22* | (2006.01) |
| *A61P 25/18* | (2006.01) |
| *A61P 25/24* | (2006.01) |
| *A61P 25/06* | (2006.01) |
| *A61K 9/00* | (2006.01) |
| *A61K 9/19* | (2006.01) |

(52) U.S. Cl.
CPC ................. *C07K 7/08* (2013.01); *A61K 9/00* (2013.01); *A61K 9/0019* (2013.01); *A61K 9/19* (2013.01); *A61P 25/06* (2018.01); *A61P 25/18* (2018.01); *A61P 25/22* (2018.01); *A61P 25/24* (2018.01); *A61P 25/28* (2018.01); *A61P 25/30* (2018.01); *A61K 38/00* (2013.01)

(58) Field of Classification Search
CPC .. C07K 7/08; A61P 25/06; A61P 25/18; A61P 25/22; A61P 25/24; A61P 25/28; A61P 25/30; A61K 9/00; A61K 9/0019; A61K 9/19; A61K 38/00
See application file for complete search history.

(56) References Cited

U.S. PATENT DOCUMENTS

| | | | |
|---|---|---|---|
| 5,972,624 A | 10/1999 | Smith et al. | |
| 10,385,098 B2 | 8/2019 | Seong | |
| 2013/0196348 A1 | 8/2013 | Leroy | |
| 2013/0345141 A1 | 12/2013 | Seong | |

FOREIGN PATENT DOCUMENTS

| | | | | |
|---|---|---|---|---|
| JP | 2008501632 A | 1/2008 | | |
| JP | 2013539975 A | 10/2013 | | |
| KR | 1020120085669 | 8/2012 | | |
| WO | WO-2005080427 A1 * | 9/2005 | ............. | A61P 25/32 |
| WO | WO-2007081792 A2 * | 7/2007 | ............. | A61P 25/28 |
| WO | WO-2012051567 A2 | 4/2012 | | |
| WO | WO-2012051657 A2 | 4/2012 | | |

OTHER PUBLICATIONS

Thundimadathil J et al. Improving stability of peptide drugs through chemical modifications. Oligos & Peptides Supplement Series, Chimica Oggi—Chemistry Today, Mar./Apr. 2014, 32(2), pp. 35-38. (Year: 2014).*

Sollenberg, U. E. et al., "M871—a Novel Peptide Antagonist Selectively Recognizing the Galanin Receptor Type 2," *International Journal of Peptide Research and Therapeutics*, vol. 12, No. 2, pp. 115-119 (2006).

Pirondi, Stefania et al., "The Galanin-R2 Agonist AR-M1896 Reduces Glutamate Toxicity in Primary Neural Hippocampal Cells," *Journal of Neurochemistry*, vol. 95, pp. 821-833 (2005).

Reyes-Alcaraz Arfaxad et al., "Development of Spexin-based Human Galanin Receptor Type II-specific Agonists with Increased Stability in Serum and Anxiolytic Effect in Mice," Scientific Reports, vol. 6, article No. 21453, pp. 1-10 (2016).

Bailey, Kathleen R. et al., "Galanin Receptor Subtype 2 (GalR2) Null Mutant Mice Display an Anxiogenic-Like Phenotype Specific to the Elevated Plus-Maze," *Pharmacology, Biochemistry and Behavior* vol. 86, pp. 8-20 (2007).

Bajo, Michal et al., "Receptor Subtype-Dependent Galanin Actions on Gamma-Aminobutyric Acidergic Neurotransmission and Ethanol Responses in The Central Amygdala," *Addiction Biology*, vol. 17, pp. 694-705 (2011).

Baranowska, B. et al., "Neuropeptide Y, Galanin, and Leptin Release in Obese Women and in Women With Anorexia Nervosa," *Metabolism*, vol. 46, No. 12, pp. 1384-1389 (1997).

(Continued)

*Primary Examiner* — Kimberly Ballard
(74) *Attorney, Agent, or Firm* — Sterne, Kessler, Goldstein & Fox P.L.L.C.

(57) ABSTRACT

The present invention relates to spexin-based agonists specific for galanin receptor type 2 and use thereof. More specifically, the present invention provides peptide-based agonists with high specificity for galanin receptor type 2 and improved stability. The peptide-based agonists are involved in the regulation of in vivo physiological functions, such as food intake, anxiety, emotion, and addiction, for which galanin receptors type 2 is responsible, to effectively suppress appetite, help recover from anxiety disorder, and reduce pleasure addiction. Therefore, the peptide-based agonists can be used to prevent or treat galanin receptor type 2-mediated diseases.

20 Claims, 29 Drawing Sheets

Specification includes a Sequence Listing.

(56) References Cited

OTHER PUBLICATIONS

Castellano, J. M. et al., "Effects Of Galanin-Like Peptide on Luteinizing Hormone Secretion in the Rat: Sexually Dimorphic Responses and Enhanced Sensitivity at Male Puberty," *Am J Physiol Endocrinol Metab* vol. 291, pp. E1281-E1289 (2006).

Einstein, Emily B. et al., "Galanin-Induced Decreases in Nucleus Accumbens/Striatum Excitatory Postsynaptic Potentials And Morphine Conditioned Place Preference Require Both Galanin Receptor 1 and Galanin Receptor 2," *European Journal of Neuroscience* vol. 37, pp. 1541-1549 (2013).

Elliott-Hunt, Caroline R. et al, "Activation of The Galanin Receptor 2 (Galr2) Protects the Hippocampus From Neuronal Damage," *Journal of Neurochemistry* vol. 100, pp. 780-789 (2007).

Gottsch, Michelle L. et al., "Phenotypic Analysis of Mice Deficient in the Type 2 Galanin Receptor (GALR2)," *Molecular And Cellular Biology* vol. 25, No. 11, pp. 4804-4811 (2005).

Gu, Liping et al., "Spexin Peptide Is Expressed In Human Endocrine And Epithelial Tissues And Reduced After Glucose Load In Type 2 Diabetes," Peptides vol. 71, pp. 232-239 (2015).

Holmes, Andrew et al., "Galanin GAL-R1 Receptor Null Mutant Mice Display Increased Anxiety-Like Behavior Specific to the Elevated Plus-Maze," *Neuropsychopharmacology* vol. 28, pp. 1031-1044 (2003).

Kim, Dong-Kyu et al., "Coevolution of the Spexin/Galanin/Kisspeptin Family: Spexin Activates Galanin Receptor Type II and III," *Endocrinology* vol. 155, pp. 1864-1873 (2014).

Lin, Cheng-yuan et al., "Spexin Enhances Bowel Movement through Activating L-type Voltagedependent Calcium Channel via Galanin Receptor 2 in Mice," *Scientific Reports* vol. 5, pp. 1-12 (2015).

Lui, Yun et al., "A novel neuropeptide in suppressing luteinizing hormone release in goldfish, Carassius auratus," *Molecular and Cellular Endocrinology* vol. 374, pp. 65-72 (2013).

Liu, Hong-Xiang et al., "Receptor Subtype-Specific Pronociceptive and Analgesic Actions of Galanin in the Spinal Cord: Selective Actions Via Galr1 And Galr2 Receptors," PNAS, vol. 98, No. 17, pp. 9960-9964 (2001).

Lu, Xiaoying et al., "Galanin (2-11) Binds to GalR3 in Transfected Cell Lines: Limitations for Pharmacological Definition of Receptor Subtypes," Neuropeptides vol. 39, pp. 165-167 (2005).

Mirabeau, Olivier et al., "Identification of Novel Peptide Hormones in the Human Proteome by Hidden Markov Model Screening," Genome Research, vol. 17, No. 3, pp. 320-327 (2007).

Rada, Pedro et al., "Ethanol Intake is Increased by Injection of Galanin in the Paraventricular Nucleus and Reduced by a Galanin Antagonist," *Alcohol* vol. 33, pp. 91-97 (2004).

Runesson, Johan et al., "A Novel GalR2-Specific Peptide Agonist," *Neuropeptides* vol. 43, pp. 187-192 (2009).

Saar, Indrek et al., "Novel Galanin Receptor Subtype Specific Ligands In Feeding Regulation," *Neurochemistry International* vol. 58, pp. 714-720 (2011).

Shi, Tie-Jun Sten et al., "Sensory Neuronal Phenotype in Galanin Receptor 2 Knockout Mice: Focus on Dorsal Root Ganglion Neurone Development and Pain Behaviour," *European Journal of Neuroscience*, vol. 23, pp. 627-636 (2006).

Swanson, Chad J. et al., "Anxiolytic- and Antidepressant-Like Profiles of the Galanin-3 Receptor ($Gal_3$) Antagonists Snap 37889 and Snap 398299," *PNAS*, vol. 102, No. 78, pp. 17489-17494 (2005).

Toll, Lawrence et al., "Peptides Derived from Die Prohormone proNPQ/spexin are Potent Central Modulators of Cardiovascular And Renal Function and Nociception," FASEB J, vol. 26, No. 2, pp. 947-954 (2012), downloaded on Apr. 3, 2018, https://www.ncbi.nlm.nih.gov/pmc/articles/PMC3290442.

Walewski, José L. et al., "Spexin is a Novel Human Peptide that Reduces Adipocyte Uptake of Long Chain Fatty Acids and Causes Weight Loss in Rodents with Diet-Induced Obesity," *Obesity (Silver Spring)*, vol. 22, No. 7, pp. 1643-1652 (2014).

Webling, Kristin E. B. et al., "Galanin Receptors and Ligands," *Frontiers in Endocrinology*, vol. 3, pp. 1-14 (2012).

Wong, Matthew K. H. et al.., "Goldfish Spexin: Solution Structure and Novel Function as a Satiety Factor in Feeding Control," *Am J Physiol Endocrinol Metab*, vol. 305, pp. E348-E366 (2013).

International Search Report of Application No. PCT/KR2016/013950, 4 pages.

Hitzeman, R. A., et al., "Isolation and characterization of the yeast 3-phosphoglycerokinase gene (PGK) by an immunological screening technique," *J. Biol. Chem* 255(24):12073-12080, American Society for Biochemistry and Molecular Biology Inc., United States (Dec. 15, 1980).

Lu, X., et al., "Phenotypic analysis of GalR2 knockout mice in anxiety- and depression-related behavioral tests," *Neuropeptides* 42(4):387-397, Churchill Livingstone, United States (Aug. 2008).

* cited by examiner

FIG. 1

|  | 1 | 2 | 3 | 4 | 5 | 6 | 7 | 8 | 9 | 10 | 11 | 12 | 13 | 14 |
|---|---|---|---|---|---|---|---|---|---|----|----|----|----|----|
| Hu_GAL: | G | W | T | L | N | S | A | G | Y | L | L | G | P | H...... |
| Hu_GALP: | G | W | T | L | N | S | A | G | Y | L | L | G | P | V...... |
| Co_SPX2: | N | W | G | P | Q | S | M | L | Y | L | K | G | R | Ya |
| Hu_SPX1: | N | W | T | P | Q | A | M | L | Y | L | K | G | A | Qa |

GAL a.a. Substitution: G, L, N, A, G, L/F, P, Ha

D a.a. Substitution: dN, dW, dT, dA, dA, dY, dL, dA, dQa

N1 Modification: p

| Substitution | GALR2 EC₅₀ (nM) | GALR2 E_max (fold induction) | GALR3 EC₅₀ (nM) | GALR3 E_max (fold induction) |
|---|---|---|---|---|
| WT | 45.7 ± 5.90 | 16.28 | 112.20 ± 14.48 | 30.77 |
| G1 | 36.31 ± 7.47 | 15.99 | 93.32 ± 20.88 | 31.64 |
| L4 | 58.88 ± 7.59 | 16.89 | 104.71 ± 17.61 | 30.52 |
| N5 | 61.66 ± 12.68 | 15.79 | 801.187 ± 184.32[b] | 34.13 |
| A7 | 38.90 ± 7.28 | 17.14 | 467.74 ± 69.63[b] | 36.69 |
| G8 | 1023.29 ± 132.04[a] | 17.28 | 1230.27 ± 108.23[a] | 35.27 |
| F11 | 48.98 ± 10.07 | 17.36 | 707.95 ± 119.10[b] | 34.29 |
| L13 | 36.31 ± 10.01 | 16.88 | 331.131 ± 61.988[b] | 40.04 |
| P13 | 38.90 ± 5.80 | 15.99 | 380.19 ± 49.06[b] | 33.63 |
| Ha14 | 53.70 ± 6.92 | 16.29 | 70.79 ± 10.54 | 32.59 |
| A7F11 | 144.54 ± 27.05 | 16.36 | >10,000 | NM |
| N5A7F11 | 107.15 ± 20.06 | 15.62 | >10,000 | NM |
| N5A7F11H14 | 54.54 ± 10.77 | 16.95 | 3019.95 ± 978.21 | 40.58 |
| N5A7F11P13(Qu) | 34.95 ± 9.24 | 16.28 | NM | NM | aP<0.05 vs. WT SPX bP<0.05 vs. potency toward GALR2. NM: not measurable

| Substitution/Modification | GALR2 EC50 (nM) | GALR2 Emax (Fold induction) | GALR3 EC50 (nM) | GALR3 Emax (Fold induction) |
|---|---|---|---|---|
| dN1 | 21.38 ± 5.54 | 15.22 | 38.90 ± 8.60 | 36.80 |
| dW2 | 100.00 ± 18.71 | 16.94 | 138.04 ± 23.22 | 33.01 |
| dT3 | NM | NM | NM | NM |
| dA4 | 97.22 ± 18.29 | 16.5 | 112.30 ± 23.07 | 27.51 |
| dA6 | 208.93 ± 26.96[a] | 17.14 | 316.23 ± 47.07[a] | 31.76 |
| dY9 | NM | NM | NM | NM |
| dL10 | NM | NM | NM | NM |
| dA12 | 1230.26 ± 158.75[a] | 17.19 | 1412.54 ± 210.27[a] | 37.2 |
| dQa14 | 77.62 ± 15.97 | 15.89 | 323.59 ± 66.55[a] | 33.88 |
| pQ1 | 35.01 ± 7.82 | 15.85 | 61.66 ± 10.37 | 33.08 |
| Ac-N1 | 56.88 ± 11.02 | 16.73 | 81.28 ± 16.71 | 31.01 |
| PEG-N1 | 61.65 ± 16.99 | 14.99 | 173.78 ± 25.87 | 31.39 |
| Cit1 | 61.66 ± 19.00 | 16.36 | 251.19 ± 64.98 | 30.40 |
| Fmoc | 77.62 ± 15.97 | 15.34 | 125.89 ± 25.89 | 31.77 |

[a]P<0.05 vs. WT SPX, NM, not measurable

| Peptide | Half-life activity (h) in FBS | Peptide | Half-life activity (h) in FBS | Half-life activity (h) in Human Serum |
|---|---|---|---|---|
| SPX | 4.1±0.5 | NSA7F11P13 (Qu) | 2.6±0.2 | 2.0±0.2 |
| Fmoc-SPX | 14.2±0.2ª | dN1-Qu | 4.2±0.1ª | 2.9±0.1ª |
| PEG-SPX | 12.5±0.5ª | PEG-Qu | 5.7±0.6ª | ND |
| Ac-N1 | 8.7±0.6ª | Fmoc-Qu | 6.1±0.2ª | 4.9±0.1ª |
| dN1 | 10.3±0.3ª | Fmoc-Qu-dQ14 | 8.4±0.3ª | 6.3±0.1ª |
| dA4 | 8.7±0.4ª | Fmoc-Qu-dA4-dQ14 | 11.8±0.2ª | 8.8±0.3ª |
| dW2 | 4.5±0.6 | PEG-Qu-dA4-dQ14 | ND | 6.0±0.2ª |
| dQ14 | 5.6±0.2ª | | | | aP<0.05 vs. WT SPX or Qu; ND, not determined

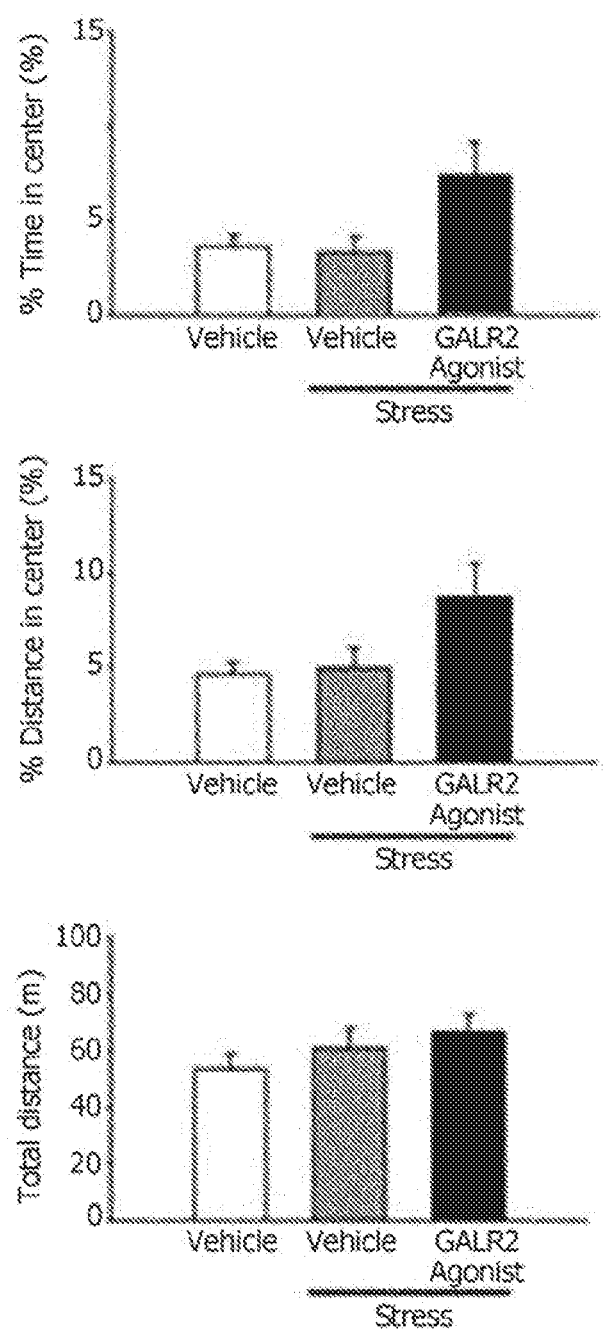

5~10min

AGONIST OF SPEXIN-BASED GALANIN TYPE 2 RECEPTOR AND USE THEREOF

CROSS-REFERENCE TO RELATED APPLICATIONS

This application is a continuation application of U.S. application Ser. No. 15/771,078, filed Apr. 25, 2018 under 35 U.S.C. § 371 (now U.S. Pat. No. 10,385,098, issued Aug. 20, 2019) and which is based on International Application No. PCT/KR2016/013950, filed Nov. 30, 2016, which claims the benefit of Korean Patent Application No. 10-2015-0168555, filed on Nov. 30, 2015, each of which is incorporated herein by reference in its entirety.

REFERENCE TO A SEQUENCE LISTING SUBMITTED ELECTRONICALLY

The content of the electronically submitted sequence listing (Name: 3763_0080002_Seqlisting_ST25.txt; Size: 17,330 bytes; and Date of Creation: Aug. 28, 2020) submitted in this application is incorporated herein by reference in its entirety.

TECHNICAL FIELD

The present invention relates to spexin-based agonists specific for galanin receptor type 2 (GALR2) and their use for preventing or treating GALR2-mediated diseases.

BACKGROUND ART

The novel neuropeptide spexin (Spexin/NQ/NPQ/SPX), which is encoded by the C12orf39 (chromosome 12 open reading frame 39) gene, was originally discovered using bioinformatics tools. The mature spexin peptide sequence consists of 14 amino acids formed as a result of cleavage of dibasic amino acids by a proprotein convertase and is very well conserved in typical vertebrate species as well as humans [Mirabeau et al., Genome Res, 2007, 17:320-327]. Spexin expression at the mRNA and/or protein level has been documented in brain regions and peripheral tissues of several species such as humans, mice, and goldfish, suggesting multiple physiological functions of spexin in vertebrates. Recently, spexin was implicated in regulation of feeding behaviors and related metabolic processes. Spexin mRNA levels are markedly decreased in the fat of obese humans, and administration of spexin leads to weight loss in diet-induced obese rodents. Spexin also suppresses appetite in goldfish. Recent reports have shown that spexin stimulates intestinal muscle contraction to induce bowel movements, is expressed in human endocrine and epithelial tissues, and is associated with glycometabolism and lipometabolism from its reduced level in patients with type 2 diabetes. In addition, spexin is likely involved in reproduction, cardiovascular/renal function, and nociception. [Waleski et al., Obesity 2014, 22:1643-1652; Wong et al., Am J Physiol Endocrinol Metab, 2013, 305:E348-366; Liu et al., Mol Cel Endocrinol, 2013, 374:65-72; Toll et al., FASEB J, 2012, 26:947-954; Lin et al., Sci Rep, 2015, 5:12095; Gu et al., Peptides, 2015, 71:232-239]. The precise roles of spexin in these processes, however, are not well understood due to a lack of information on the spexin receptor. Recently, the present inventors demonstrated that spexin is an endogenous ligand that acts at galanin receptor (hereinafter referred to as "GALR") types 2 and 3 but not at GALR1, while galanin activates all three receptor subtypes. Indeed, it can be considered that galanin shares activity on GALR2 in common with spexin because of its very low potency for GALR3 [Kim et al., Endocrinology, 2014, 155:1864-1873].

The spexin and galanin genes likely emerged through a local duplication from a common ancestor gene, and as a result, their mature peptides share several conserved residues, including $Trp^2$, $Thr^3$, $Tyr^9$, and $Gly^{12}$ [Kim et al., Endocrinology, 2014, 155:1864-1873]. Like spexin, galanin is widely expressed in the central nervous system and peripheral tissues. The actions of spexin and galanin in appetite behavior and reproduction, however, appear to oppose each other. For instance, levels of galanin are significantly higher in obese women, and galanin administration or overexpression in genetically engineered mice results in an increase in food intake. Thus, galanin appears to be orexigenic, while spexin is anorexic. Administration of galanin-like peptide stimulates luteinizing hormone (LH) secretion, while spexin administration attenuates LH secretion in the goldfish [Barnowska et al., Metabolism, 1997, 46:1384-1389; Rada et al., Alcohol, 2004, 33:91-97; Castellano et al., Am J Physiol Endocrinol Metab, 2006, 291: E1281-1289; Liu et al., Mol Cel Endocrinol, 2013, 374:65-72]. These opposing effects are likely due to GALR receptor subtype-specific signaling pathways. Specifically, GALR1 and GALR3 induce inhibitory $G_i$-coupled signaling, while GALR2 triggers stimulatory Gq-coupled signaling [Webling et al., Front Endocrinol, 2012, 3:146].

Studies on GALR2-mediated phenotypes have been made through attempts to develop receptor gene knockout (KO) mice and agonists and antagonists selectively acting on the receptor. In GALR2 KO mice, no unusual abnormalities with respect to sensory function, feeding behavior, reproduction, mood, learning and memory were reported. Later then, anxiety- and depression-related behaviors were demonstrated in GALR2 KO mutants. This phenotype was similar to that observed in GALR1 KO mice; however, this GALR2-mediated effect is likely the opposite of the GALR3 effect, as GALR3-specific antagonists decrease anxiety and induce depression-like behavior [Gottsch et al., Mol Cell Biol, 2005, 25:4804-4811; Bailey et al., Pharmacol Biochem Behav, 2007, 86:8-20; Lu et al., Neuropeptides, 2008, 42:387-397; Holmes et al., Neuropsychopharmacology, 2003, 28:1031-1044; Swanson et al., Proc Natl Acad Sci USA, 2005, 102:17489-17494]. GALR2 deficiency resulted in developmental loss of dorsal root ganglion neurons and microinjection of a GALR2-specific agonist into the spinal cord induced allodynic effects, suggesting a possible role in pain behavior. Involvement of GALR2 in the mesolimbic reward system has been reported; galanin decreases the amplitude of excitatory postsynaptic potential in dorsal striatum and nucleus accumbens, and this effect is absent in GALR2 KO mice. In the central amygdala, galanin, through binding of the GALR2, decreases the amplitudes of GABAergic inhibitory postsynaptic potentials. Activation of GALR2 protects the hippocampus from neuronal damage through the phosphorylation of the serine/threonine kinase Akt [Shi et al., Eur J Neurosci, 2006, 23:627-636; Liu et al., Proc Natl Acad Sci USA, 2001, 98:9960-9964; Einstein et al., Eur J Neurosci 2013, 37:1541-1549; Bajo et al., Addict Biol, 2012, 17:694-705; Elliotte-Hunt et al., J Neurochem, 2007, 100:780-789]. Such GALR2-mediated phenomena function in opposition, in concert, or independently of GALR1 and GALR3-mediated phenomena. Nevertheless, these observations suggest the possible involvement of GALR2s in learning and memory, pain, anxiety, and mood disorders.

Several attempts have been made to develop GALR receptor subtype-specific agonists. A galanin fragment consisting of the amino acid residues at positions 2-11 of galanin, GAL (2-11), was first developed as a GALR2 selective agonists, but further studies unfortunately revealed that this fragment has similar affinity for the GALR3. Several GALR2-specific agonists, which were generated by modification at the N-terminus and/or C-terminus of galanin, have been reported over the years. Of these, M1145 and M1153 were found to exhibit GALR2 selectivity with 50-100-fold binding preference for GALR2 compared to GALR1 and GALR3; however, at high concentrations, these agonists retain substantial affinity for GALR1 and GALR3 [Liu et al., Proc Natl Acad Sci USA, 2001, 98:9960-9964; Lu et al., Neuropeptides, 2005, 39:165-167; Webling et al., Front Endocrinol, 2012, 3:146; Runesson et al., Neuropeptides, 2009, 43:187-192; Saar et al., Neurochrm Int, 2011, 6:714-720].

Despite numerous efforts to develop several species of galanin receptor subtype-specific agonists in the previous studies, treatment with high concentrations of the agonists was found to cause specificity problems. Under these circumstances, there arises a need to elucidate GALR subtype-specific mediated physiological functions in the development of receptor subtype-specific agonists.

Thus, the present inventors have succeeded in developing improved agonists by identifying the reactivity between spexin and GALR2 through sequencing and substitution of the constituent amino acids of galanin and spexin and increasing the stability of the agonists, and in elucidating the physiological functions of the agonists when administered to animals, achieving the present invention.

DETAILED DESCRIPTION OF THE INVENTION

Problems to be Solved by the Invention

The present invention is aimed at providing peptide-based galanin receptor type 2 agonist with enhanced selectivity for galanin receptor type 2 and increased stability in blood.

The present invention is also aimed at providing the pharmaceutical use of the peptide-based galanin receptor type 2 agonists for preventing or treating galanin receptor type 2-mediated diseases.

Means for Solving the Problems

One aspect of the present invention provides a peptide-based galanin receptor type 2 agonist having the amino acid sequence set forth in formula 1:

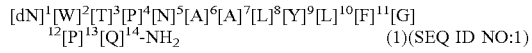

wherein one or more amino acids in formula 1 are optionally substituted; and wherein, in formula 1, $[dN]^1$ represents D-asparagine and may be replaced with one of pyroglutamate (pQ), citrulline (Cit), L-asparagine (N), and glycine (G) or may be replaced with asparagine protected with polyethylene glycol (PEG), an acetyl (Ac) group or Fmoc, $[W]^2$ may be replaced with D-tryptophan (dW) or a 2-naphtyl group, $[T]^3$ may be replaced with alanine (A) or lysine (K), $[P]^4$ may be replaced with D-alanine (dA) or D-valine (dV), $[N]^5$ may be replaced with glutamine (Q), $[A]^6$ may be replaced with D-alanine (dA), $[A]^7$ may be replaced with methionine (M), $[F]^{11}$ may be replaced with lysine (K), leucine (L) or tyrosine (Y), $[P]^{13}$ may be replaced with D-alanine (dA) or alanine (A), $[Q]^{14}$ may be replaced with D-glutamine (dQ) or histidine (H).

Preferably, the agonist has any one of the amino acid sequences set forth in formulas: 2 to 4:

(2)

(3)

(4)

A further aspect of the present invention provides a composition for preventing or treating a galanin receptor type 2-mediated disease including the peptide-based galanin receptor type 2 agonist.

Another aspect of the present invention provides a method for preventing or treating a galanin receptor type 2-mediated disease including administering a pharmaceutically effective amount of the composition to a subject in need of such prevention or treatment.

Effects of the Invention

The peptide-based agonists of the present invention have high specificity for galanin receptor type 2 and improved stability. The peptide-based agonists are involved in the regulation of in vivo physiological functions, such as food intake, anxiety, emotion, and addiction, for which galanin receptors type 2 is responsible, to effectively suppress appetite, help recover from anxiety disorder, and reduce pleasure addiction. Therefore, the peptide-based agonists can be used to prevent or treat galanin receptor type 2-mediated diseases.

BRIEF DESCRIPTION OF THE DRAWINGS

FIG. 1 compares the amino acid sequences of both human spexin ("Hu_SPX1"; SEQ ID NO: 6) and coelacanth spexin ("Co_SPX2"; SEQ ID NO: 5) with that of human galanin ("Hu_GAL"; SEQ ID NO: 3) and human galanin-like peptide ("Hu_GALP"; SEQ ID NO: 4), and shows mutation positions and modifications of the amino acids in the sequences.

FIGS. 2A and 2B are lists of spexin-based mutant peptides whose sequences include mutation, substitution, and modification of one or more amino acids. In FIG. 2A, the following sequences are provided: (1) h/m SPX (SEQ ID NO: 8); (2) [dN']-SPX (SEQ ID NO: 9); (3) [pQ']-SPX (SEQ ID NO: 10); (4) [Ac-N¹]-SPX (SEQ ID NO: 11); (5) [G¹]-SPX (SEQ ID NO: 12); (6) [dW²]-SPX (SEQ ID NO: 13); (7) [2Nal²]-SPX (SEQ ID NO: 14); (8) [dT³]-SPX (SEQ ID NO: 15); (9) [A³]-SPX (SEQ ID NO: 16); (10) [K³]-SPX (SEQ ID NO: 17); (11) [dA⁴]-SPX (SEQ ID NO: 18); (12) [E⁴]-SPX (SEQ ID NO: 19); (13) [L⁴]-SPX (SEQ ID NO: 20); (14) [R⁴]-SPX (SEQ ID NO: 21); (15) [dV⁴]-SPX (SEQ ID NO: 22); (16) [N⁵]-SPX (SEQ ID NO: 23); (17) [dA⁶]-SPX (SEQ ID NO: 24); (18) [A⁷]-SPX (SEQ ID NO: 25); (19) [G⁸]-SPX (SEQ ID NO: 26); (20) [Q⁸]-SPX (SEQ ID NO: 27); (21) [F⁹]-SPX (SEQ ID NO: 28); (22) [dY⁹]-SPX (SEQ ID NO: 29); (23) [dL¹⁰]-SPX (SEQ ID NO: 30); (24) [F¹¹]-SPX (SEQ ID NO: 31); (25) [L¹¹]-SPX (SEQ ID NO: 32); and (26) [Y¹¹]-SPX (SEQ ID NO: 33). In FIG. 2B, the following sequences are provided: (27) [dK¹¹]-SPX (SEQ ID NO: 34); (28) [ΔK¹¹]-SPX (SEQ ID NO: 35); (29) [D¹¹]-SPX (SEQ ID NO: 36); (30) [dA¹²]-SPX (SEQ ID NO: 37); (31) [dA¹³]-SPX (SEQ ID NO: 38); (32) [P¹³]-SPX (SEQ ID NO: 39); (33) [dQ¹⁴]-SPX (SEQ ID NO: 40); (34) [H¹⁴]-SPX (SEQ ID NO: 41); (35) [PEG]-SPX (SEQ ID NO: 42); (36) Cyclic-SPX (SEQ ID NO: 43); (37) [Cit¹]-SPX (SEQ ID NO: 44); (38) [Fmoc]-SPX (SEQ ID NO: 45); (39) [Fmoc-dT³]-SPX (SEQ ID NO: 46); (40) SPX-M40 (SEQ ID NO: 47); (41) [A⁷][F¹¹]-SPX (SEQ ID NO: 48); (42) [R¹¹][F¹²]-SPX (SEQ ID NO: 49); (43) [N⁵][A⁷][F¹¹]-SPX (SEQ ID NO: 50); (44) [N⁵][A⁷][F¹¹][P¹³]-SPX (SEQ ID NO: 51); (45) [N⁵][A⁷][F¹¹][H¹⁴]-SPX (SEQ ID NO: 52); (46) PEG2-SPX (SEQ ID NO: 53); (47) [3-NO2_Y9]-SPX (SEQ ID NO: 54); (48) [Fmoc-Qu]-SPX (SEQ ID NO: 55); (49) [Fmoc-Qu-dQ¹⁴]-SPX (SEQ ID NO: 56); (50) [Fmoc-Qu-dA⁴]-SPX (SEQ ID NO: 57); (51) [Fmoc-Qu-dA⁴-dQ¹⁴]-SPX (SEQ ID NO: 58); and (52) [PEG-Qu-dA⁴-dQ¹⁴]-SPX (SEQ ID NO: 59).

FIG. 4 shows quantified potencies of spexin-based mutant peptides toward GALR2 and GALR3.

FIGS. 13A and 13B shows the times in center (%), distances in center (%), and total distances for 10 min (0-5 min in FIG. 13A and 5-10 min in FIG. 13B) for experimental animals, which were measured by the open field test (OFT) to investigate the therapeutic effect of a GALR2 agonist on movement and anxiety of the animal models.

BEST MODE FOR CARRYING OUT THE INVENTION

Figure 3A:
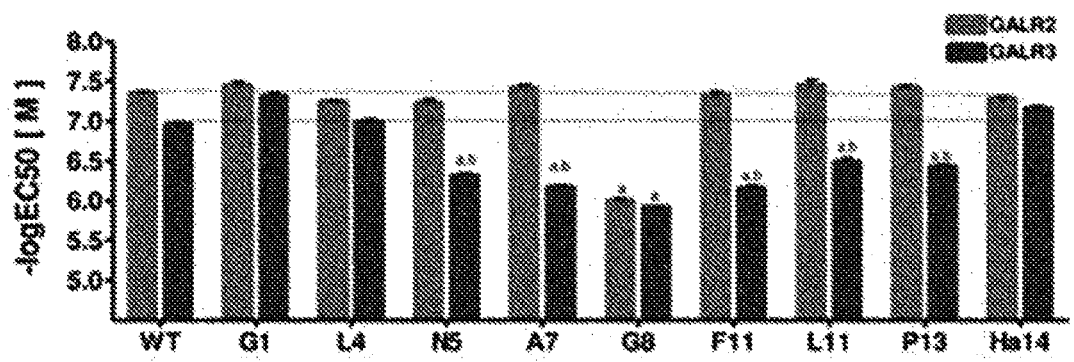
FIG. 3A shows potencies of spexin-based single mutant peptides toward GALR2 and GALR3.
Figure 3B:
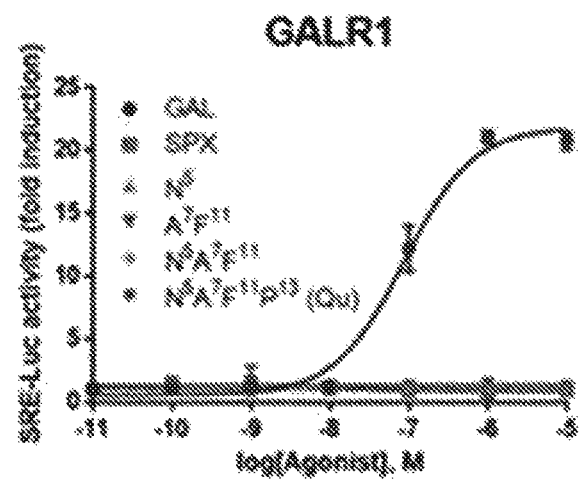
FIG. 3B shows potencies of spexin-based single (N⁵), double (A⁷F¹¹), triple (N⁵A⁷F¹¹), and quadruple (N⁵A⁷F¹¹P¹³) mutant peptides toward GALR1.
Figure 3C:
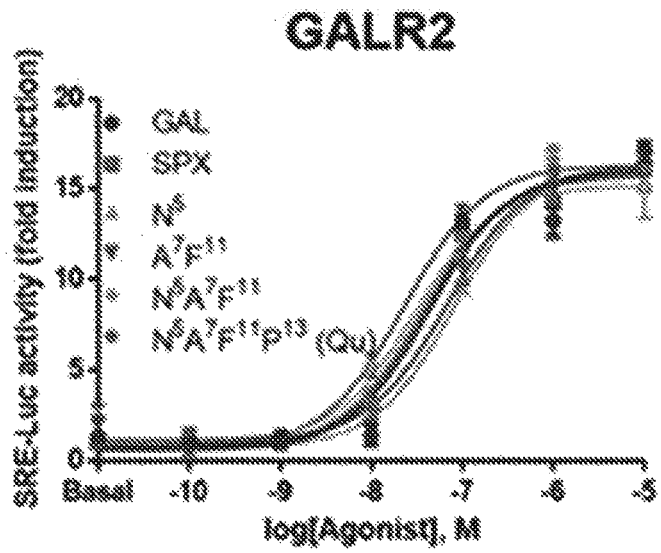
FIG. 3C shows potencies of spexin-based single (N⁵), double (A⁷F¹¹), triple (N⁵A⁷F¹¹), and quadruple (N⁵A⁷F¹¹P¹³) mutant peptides toward GALR2.
Figure 3D:
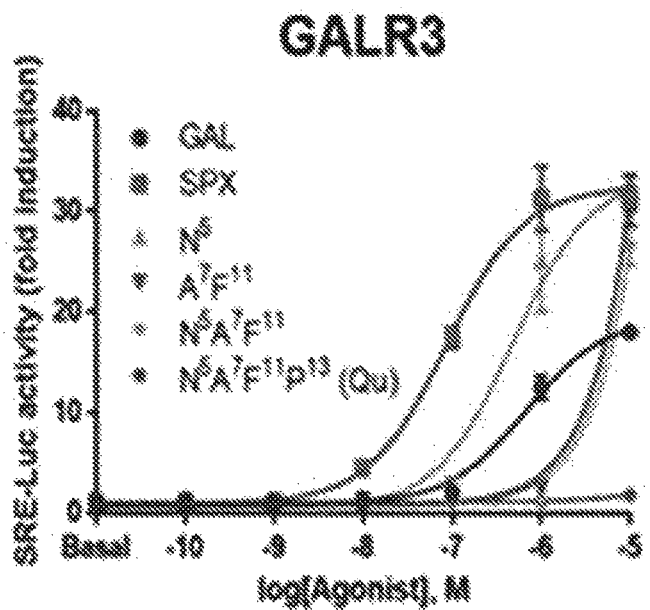
FIG. 3D shows potencies of spexin-based single (N⁵), double (A⁷F¹¹), triple (N⁵A⁷F¹¹), and quadruple (N⁵A⁷F¹¹P¹³) mutant peptides toward GALR3.

The present invention will now be described in detail.

The present invention is directed to a peptide-based galanin receptor type 2 agonist having the amino acid sequence set forth in formula 1:

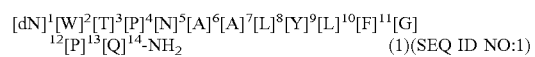

(1)(SEQ ID NO:1)

wherein one or more amino acids in formula 1 are optionally substituted; and wherein, in formula 1, [dN]¹ represents D-asparagine and may be replaced with one of pyroglutamate (pQ), citrulline (Cit), L-asparagine (N), and glycine (G) or may be replaced with asparagine protected with polyethylene glycol (PEG), an acetyl (Ac) group or Fmoc,

[W]² may be replaced with D-tryptophan (dW) or a 2-naphtyl group,

[T]³ may be replaced with alanine (A) or lysine (K),

[P]⁴ may be replaced with D-alanine (dA) or D-valine (dV),

[N]⁵ may be replaced with glutamine (Q),

[A]⁶ may be replaced with D-alanine (dA),
[A]⁷ may be replaced with methionine (M),
[F]¹¹ may be replaced with lysine (K), leucine (L) or tyrosine (Y),
[P]¹³ may be replaced with D-alanine (dA) or alanine (A),
[Q]¹⁴ may be replaced with D-glutamine (dQ) or histidine (H).

Preferably, the agonist has any one of the amino acid sequences set forth in formulas: 2 to 4:

(2)
dNWTPNAALYLFGPQ-NH₂

(3)
PEG-NWTdANAALYLFGPdQ-NH₂

(4)
Fmoc-NWTdANAALYLFGPdQ-NH₂

The galanin receptor type 2 agonist of the present invention selectively acts on galanin receptor type 2 (hereinafter referred to as 'GALR2') and is long-acting.

In the Examples section that follows, galanin and spexin present in various vertebrate species were confirmed to share tryptophan at position 2 [Trp²], tyrosine at position 9 [Tyr⁹], leucine at position 10 [Lee], and glycine at position 12 [Gly"] in common when their amino acid sequences were compared. Mutant peptides were prepared by replacing the same amino acids of spexin and galanin with the corresponding D-amino acids. Mutant peptides were prepared by replacing the specific amino acids of spexin with the corresponding amino acids of galanin. Mutant peptides were prepared by replacing the 14 amino acids of spexin with different amino acids or the corresponding D-amino acids. Changes in the activity of the mutant peptides on galanin receptors were observed.

The HEK293-G_{qi} stable cell line was employed to observe changes in the activity of the mutant peptides on galanin receptors. The HEK293-G_{qi} stable cell line is a cell line in which the C-terminus of G_q is substituted with 3 amino acids of G to convert the signals of G to G_q signaling pathways. G proteins are heterotrimers, each of which consists of α-, β-, and γ-subunits. The α-subunit is involved in intracellular signal transduction. The α-subunit may be of s-type (Gas), i-type (Gai) or q/11-type. The s-type α-subunit activates adenyl cyclase as an intracellular enzyme to produce cAMP, the universal second messenger, from ATP and activates protein kinase A (PKA). In contrast, the i-type α-subunit sends signals suppressing the activity of adenyl cyclase and the q/11-type α-subunit increases the intracellular level of calcium or activates protein kinase C (PKC). GALR subtypes 1 and 3 induce inhibitory G-coupled signaling, while GALR subtype 2 triggers stimulatory G_q-coupled signaling. This difference explains the use of the HEK293-G_{qi} stable cell line in which the C-terminus of G_q is substituted with 3 amino acids of G to convert the signals of G_i to G_q signaling pathways.

When changes in the activity of the mutant peptides on galanin receptors were measured, the quadruple mutant (N⁵A⁷F¹¹P¹³ or Qu) in which the amino acids at positions 5, 7, 1, and 13 (alanine) were replaced with asparagine [Asn⁵], alanine [Ala'], phenylalanine [Phe¹¹], and proline [Pro¹³], respectively, maintained its potency toward GALR2 at a level comparable to that of spexin but lost its potency toward GALR3 (see FIGS. 3A to 3D and FIG. 4). The introduction of the amino acids of galanin into spexin did not induce the potency toward GALR1, indicating specificity of the corresponding amino acids for the activation of GALR2.

Figure 5A:
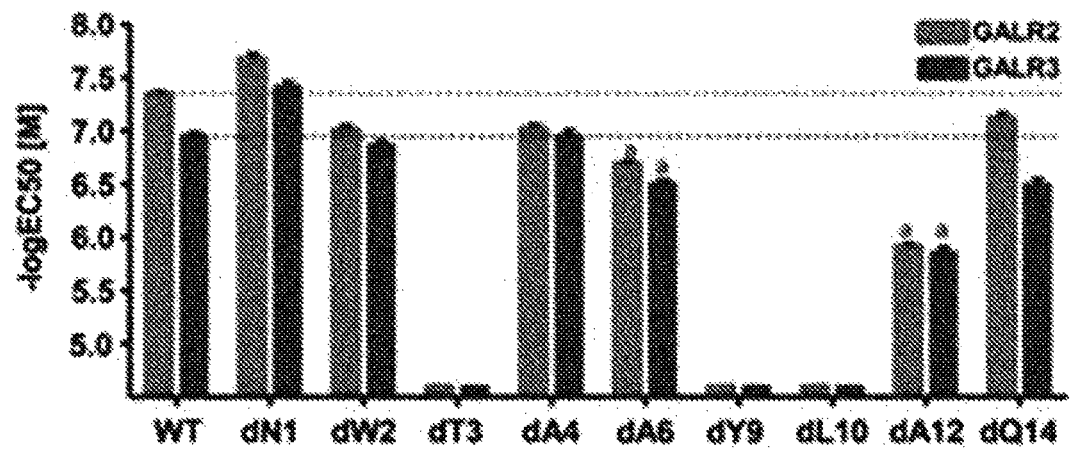
FIG. 5A shows potencies of D-amino acid-substituted spexin-based mutant peptides toward GALR2 and GALR3.
Figure 5B:
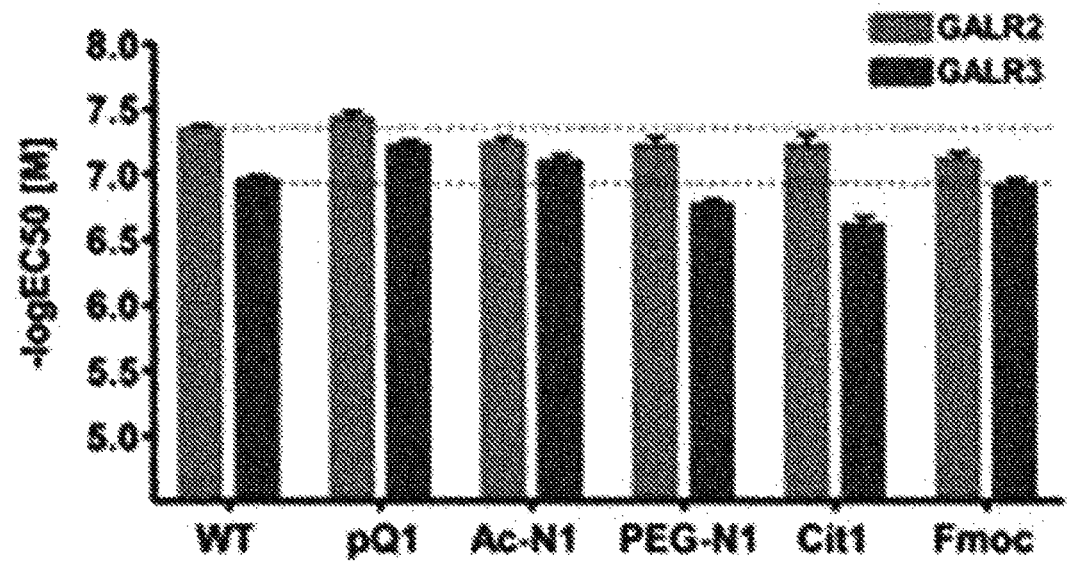
FIG. 5B shows potencies of [Asn¹]-substituted/modified spexin-based mutant peptides toward GALR2 and GALR3.
Figures 6, 7A:
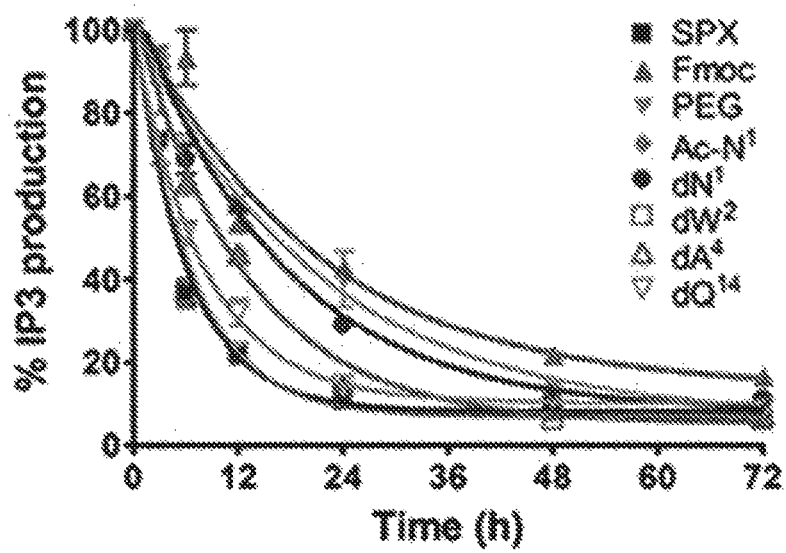
FIG. 6 shows quantified potencies of D-amino acid-substituted and [Asn¹]-substituted/modified spexin-based mutant peptides toward GALR2 and GALR3.
FIG. 7A shows stabilities of spexin-based mutant peptides in the presence of 100% PBS.

The purpose of D-amino acid substitution is to identify important residues that are responsible for receptor activation and to protect the peptide from attacks by a large variety of proteases present in serum. The D-amino acid substitution of the amino acids at other positions except the amino acid at position 1 of spexin resulted in a loss of potency toward the galanin receptors. However, the substitution of asparagine at position 1 [Asn¹] of spexin with the corresponding D-amino acid [dN¹] slightly increased the potency toward both GALR2 and GALR3 (FIGS. 5A and 5B and FIG. 6). Such changes show that the substitution of the amino acid at position 1 of spexin affords the possibility of developing stable agonists against proteases in serum.

Thus, asparagine at position 1 [Asn¹] of spexin was replaced with pyroglutamate (pQ), citrulline (Cit), Fmoc, etc. or the N-terminus of spexin was polyethylene glycosylated (PEG) or acetylated. Such modifications had no influence on the potencies toward GALR2 and GALR3, similarly to the D-amino acid substitutions (FIGS. 5A and 5B, and FIG. 6). This strongly suggests that the substitution of the amino acid at position 1 of spexin increases the stability against proteases in serum while having no influence on the potency toward GALR.

In the Examples section that follows, the potencies of the peptide-based GALR2 agonists of the present invention toward GALR2 in serum were determined via IP3 production in GALR2-expressing cells to investigate the stability of the peptide-based GALR2 agonists.

As a result, it was found that the potency of spexin was reduced very rapidly to 80% or less within 12 h but the mutant peptides underwent less reduction in IP3 production than spexin (FIGS. 7A to 7E and 8) and were more slowly degraded in serum than spexin, indicating their better stability in serum. Thus, a quadruple mutant (dN1-Qu) and sextuple mutants (PEG-QudA⁴dQ¹⁴ (PEG-se) and Fmoc-QudA⁴dQ (Fmoc-se)) with increased stability and specificity for GALR2 were finally developed (FIGS. 7A to 7E and 8).

The effects of the GALR2 agonists were investigated by the following procedure. First, a cannula was inserted into the third ventricle of animal models. After administration of each GALR2 agonist, changes in the weight and diet of the animals were compared. As a result, the food intake was significantly decreased in the animal models administered the GALR2 agonist compared to in the animal models administered spexin. This feed intake decrease induced a weight loss (FIGS. 9A to 9D). The GALR2 agonist was found to be effective in decreasing feed intake and body weight in a concentration-dependent manner. The effects of the GALR2 agonist disappeared by the administration of commercially available GALR2 antagonist M871 (FIGS. 9E to 9F).

Figure 10:
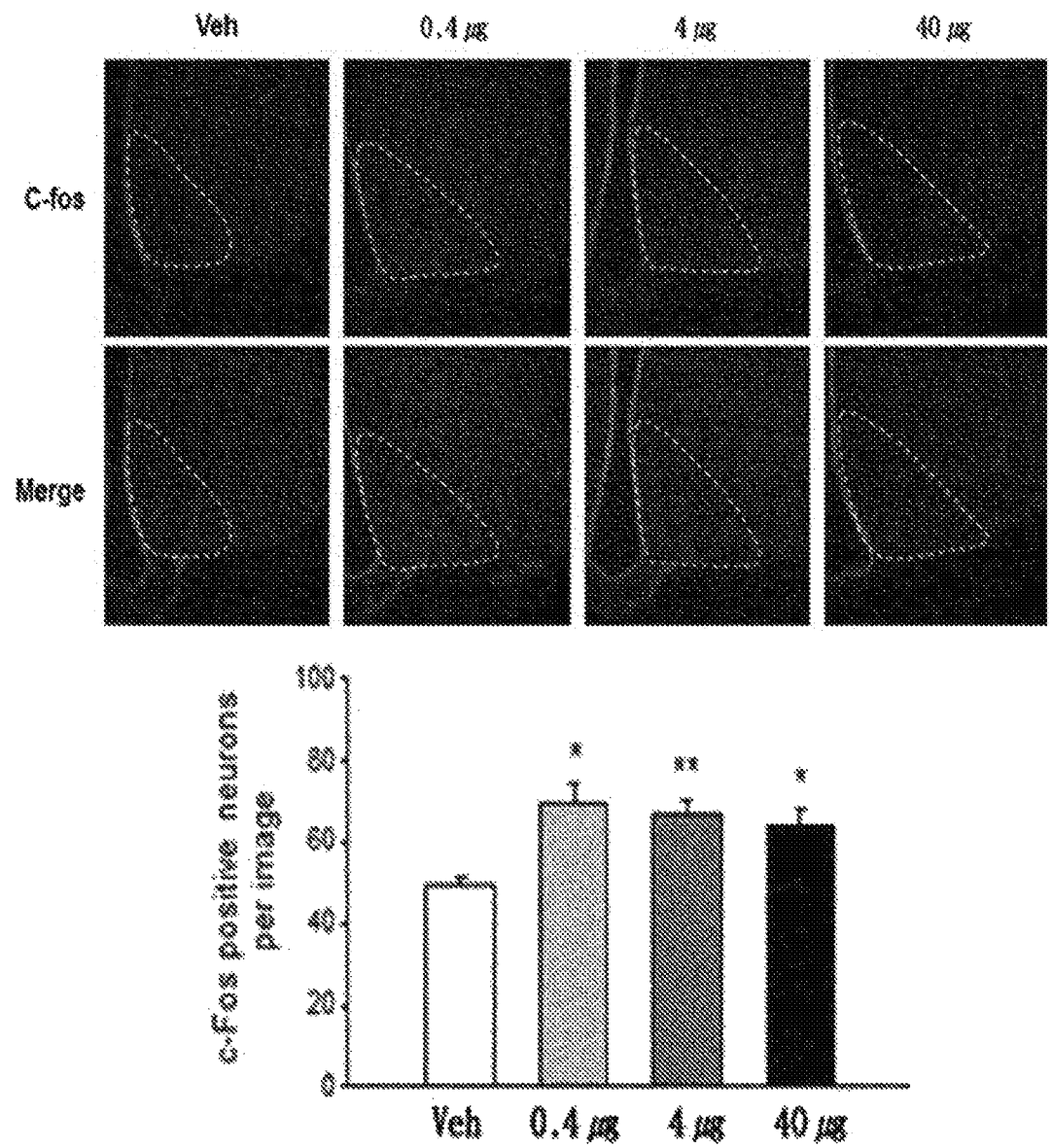
FIG. 10 shows an increase in the activity of neurons in the arcuate nucleus by treatment with different concentrations of a GALR2 agonist.

The administration of the GALR agonist to the ventricle was found to increase the activity of neurons in the arcuate nucleus known to regulate appetite through c-fos antibody (FIG. 10).

Figure 11A:
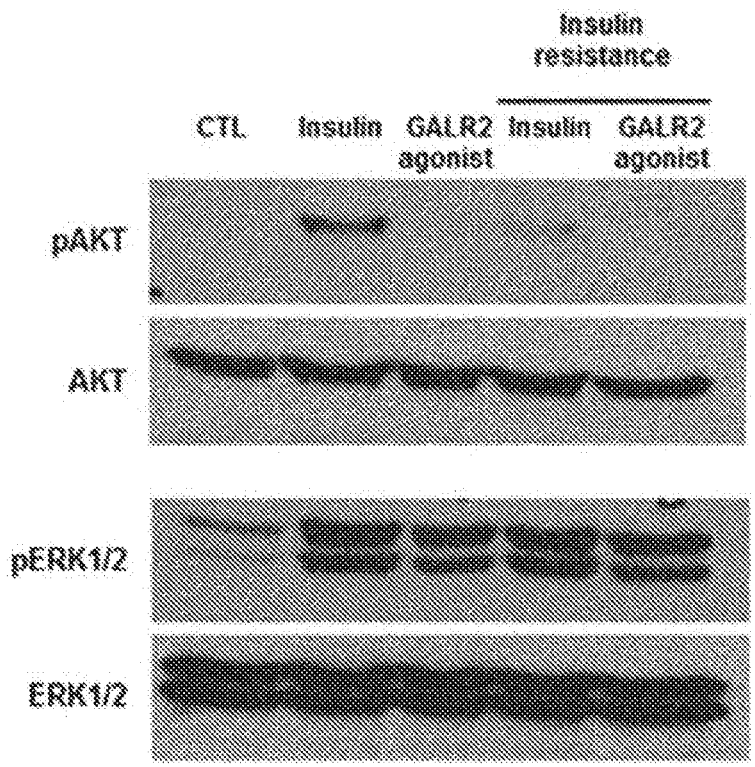
FIG. 11A shows regulatory effects of a GALR2 agonist on intracellular signaling.
Figure 11B:
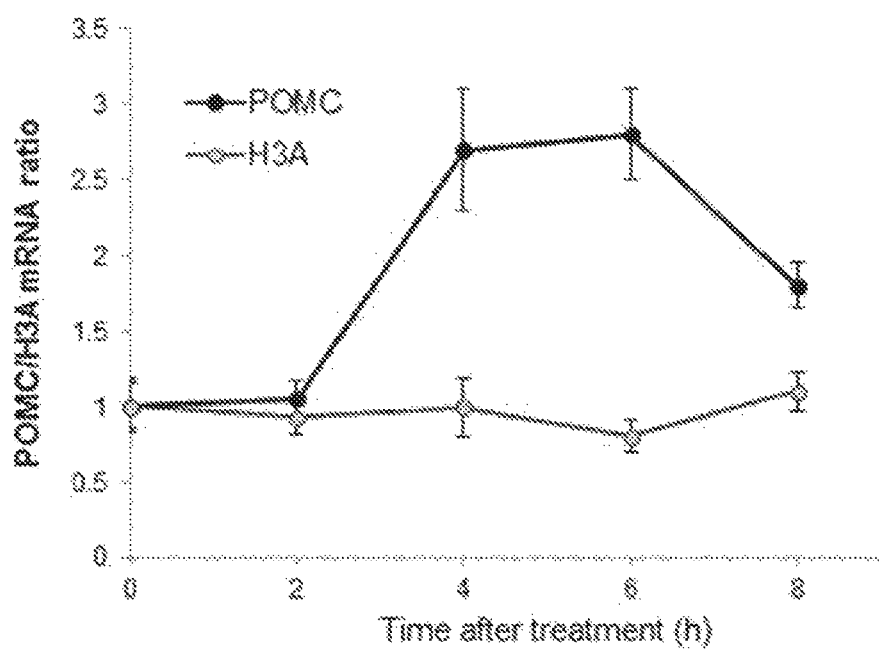
FIG. 11B shows stimulatory effects of a GALR2 agonist on POMC gene expression.
Figure 11C:
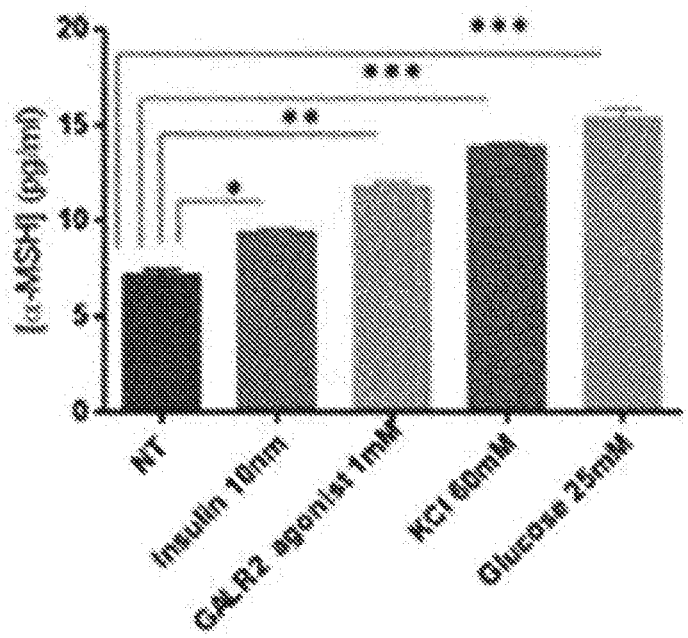
FIG. 11C shows regulatory effects of a GALR2 agonist on -MSH secretion.
Figure 11D:
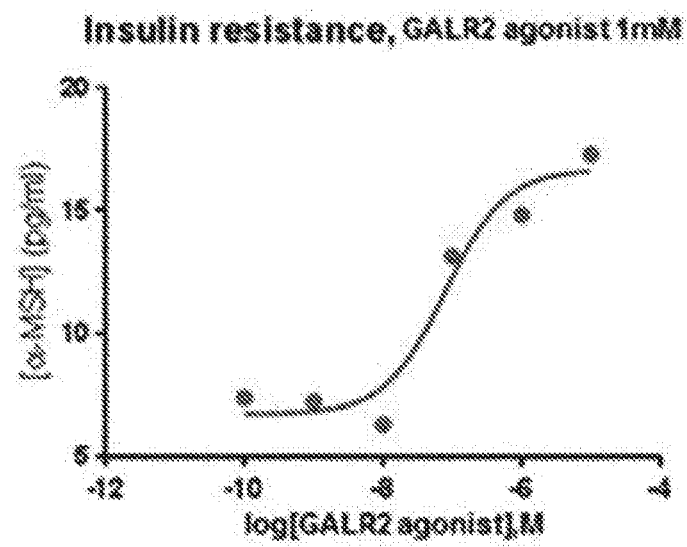
FIG. 11D shows regulatory effects of a GALR2 agonist on -MSH secretion in insulin resistance.
Figure 11E:
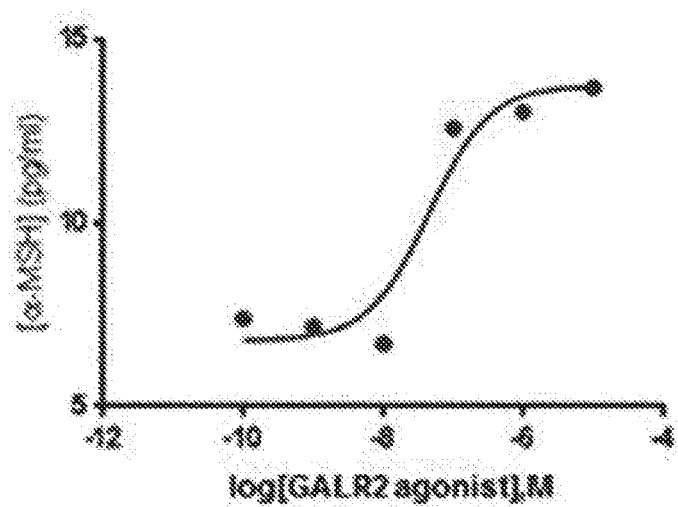
FIG. 11E shows regulatory effects of a GALR2 agonist at different concentrations on -MSH secretion.

When POMC neurons known to regulate feeding in the brain were cultured in vitro and treated with the GALR2 agonist, the pERK pathway was phosphorylated. This is different from the insulin-induced effect, indicating that the GALR2-induced effect acts through a pathway different from the insulin-induced effect (FIG. 11A). In addition, the POMC gene and a-MSH were increased by treatment with the GALR2 agonist (FIGS. 11B to 11E).

Therefore, the GALR2 agonist can be used as a drug that suppresses feeding behaviors to treat obesity.

Figure 13B:
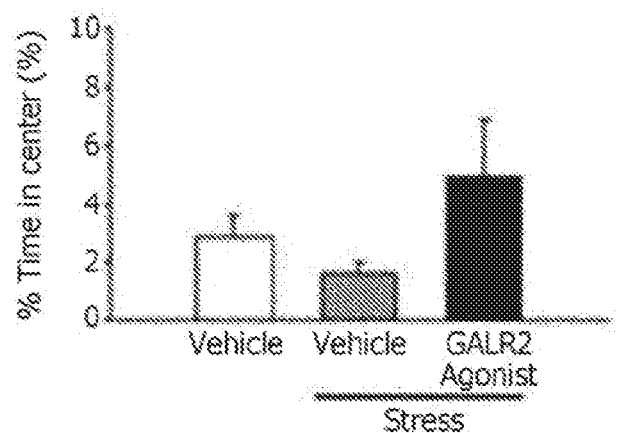
Figure 13B:
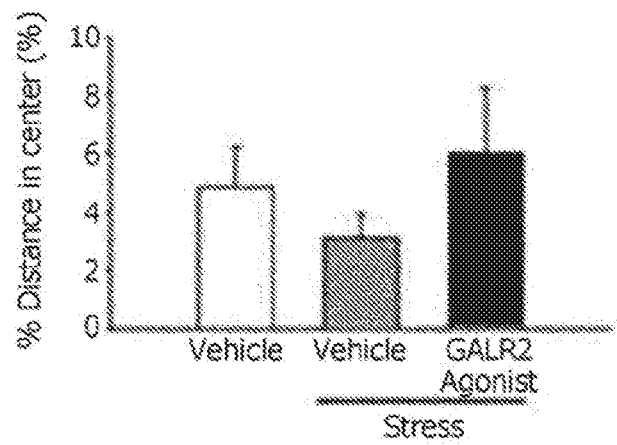
Figure 13B:
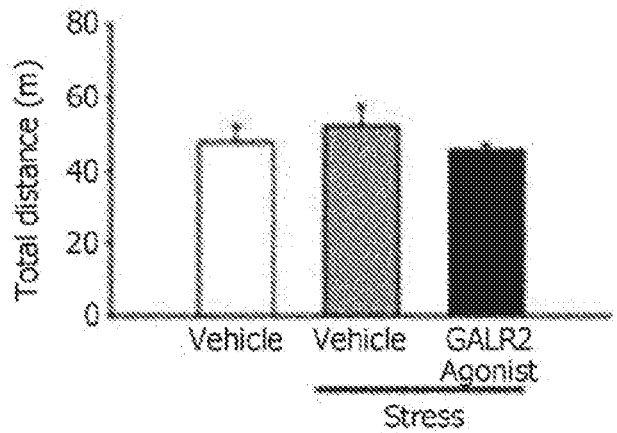
Figure 14:
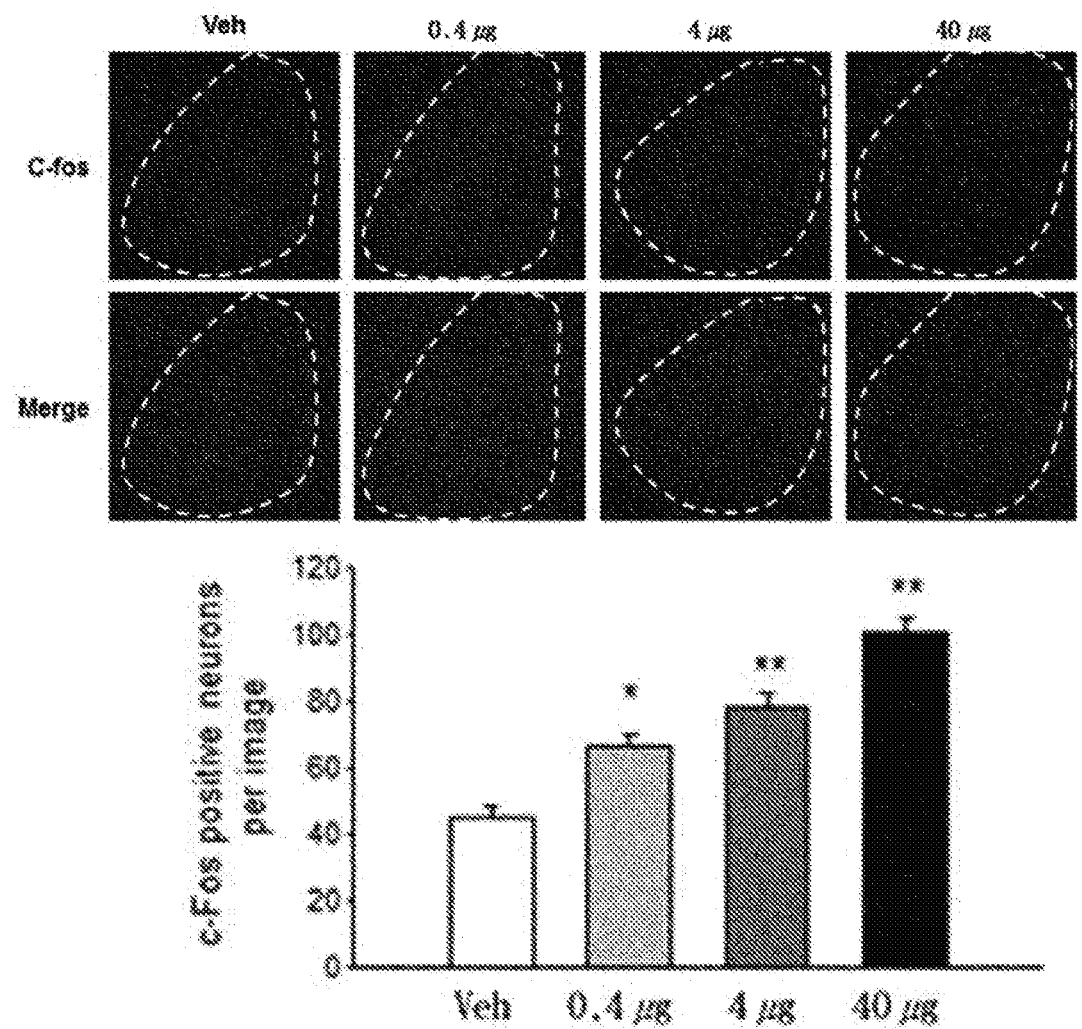
FIG. 14 shows an increase in the activity of neurons in the amygdala by treatment with different concentrations of a GALR2 agonist.
Figure 15A:
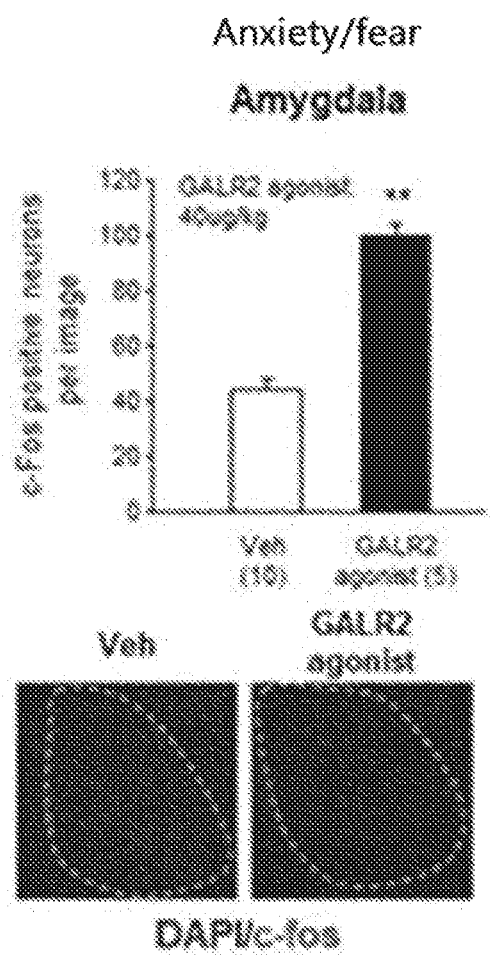
FIGS. 15A to 15D show increases in the activity of neurons in brain regions other than the amygdala by treatment with a GALR2 agonist.
Figure 15B:
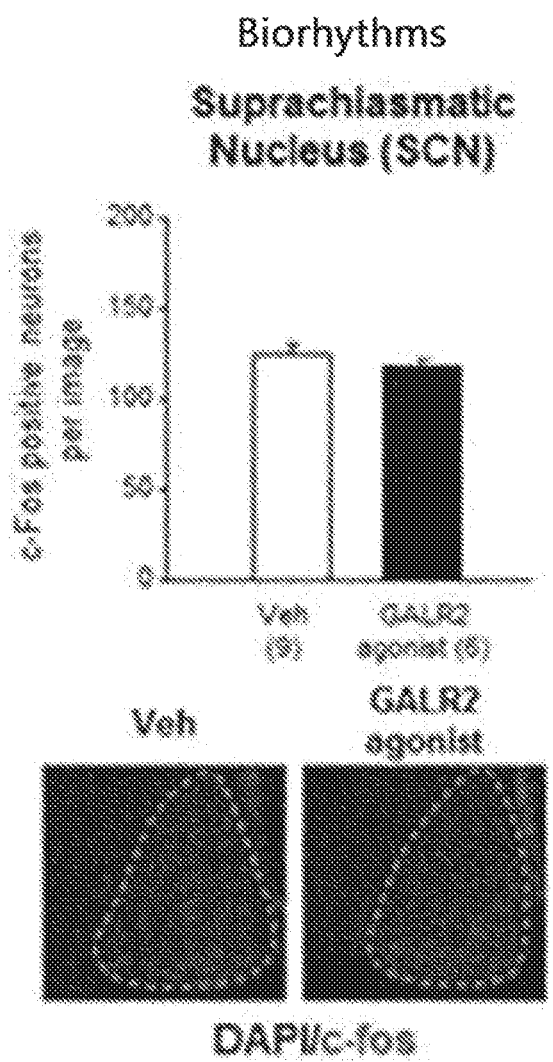
Figure 15C:
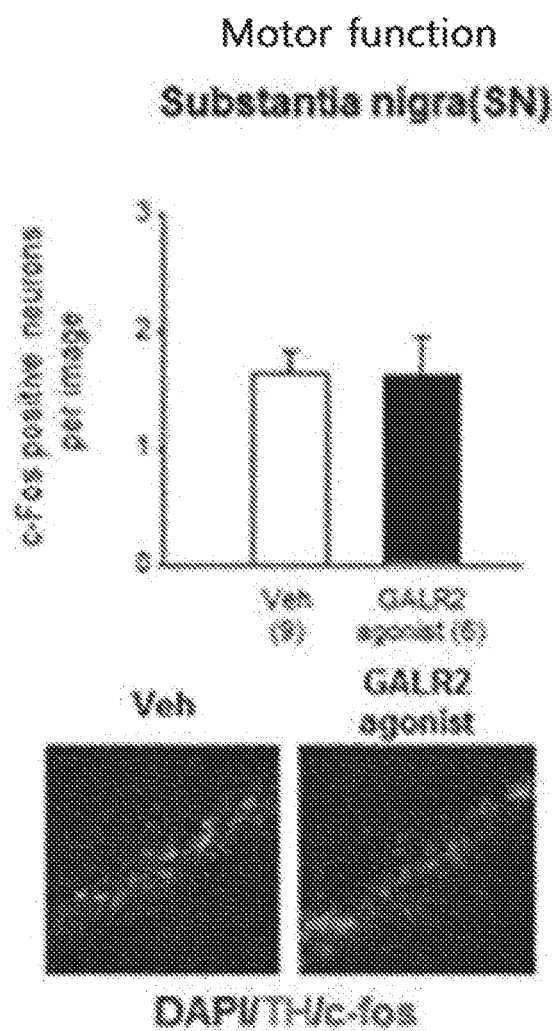
Figure 15D:
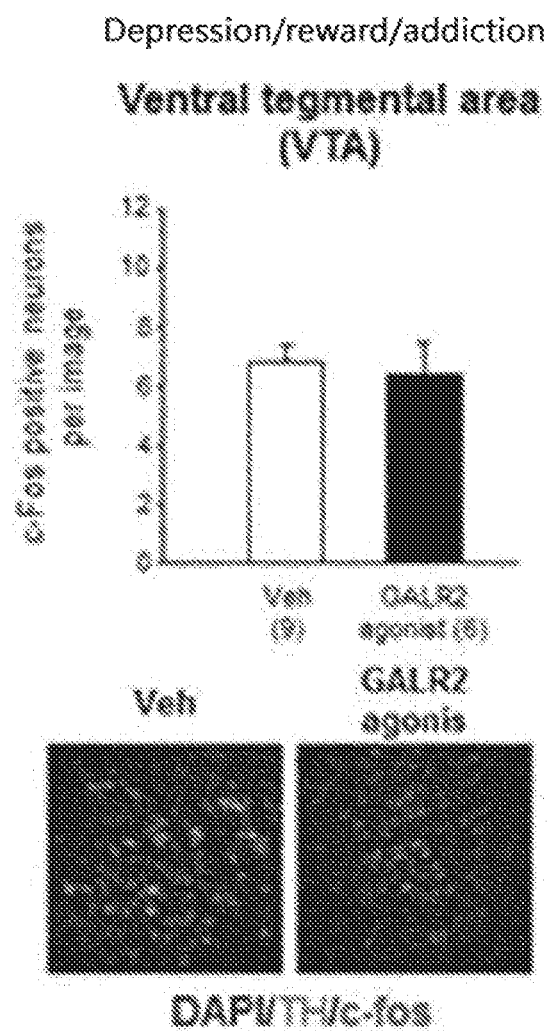

Next, the effect of the GALR2 agonist on recovery from anxiety disorder was investigated. To this end, a cannula was inserted into the lateral ventricle of animal models and the EPM test was conducted to measure anxiety/obsession. When the GALR2 agonist was administered, there was a difference in the number of center crossing but anxiety was reduced (FIG. 12), which were also demonstrated by the OFT (FIG. 13). An increase in the activity of neurons was observed in the amygdala, an anxiety-regulating brain region, when the GALR2 agonist was administered (FIG. 14). There was no increase in the activity of neurons in other brain regions (FIG. 15). Therefore, the GALR2 agonist can be used as a drug for treating anxiety disorder.

Figure 16:
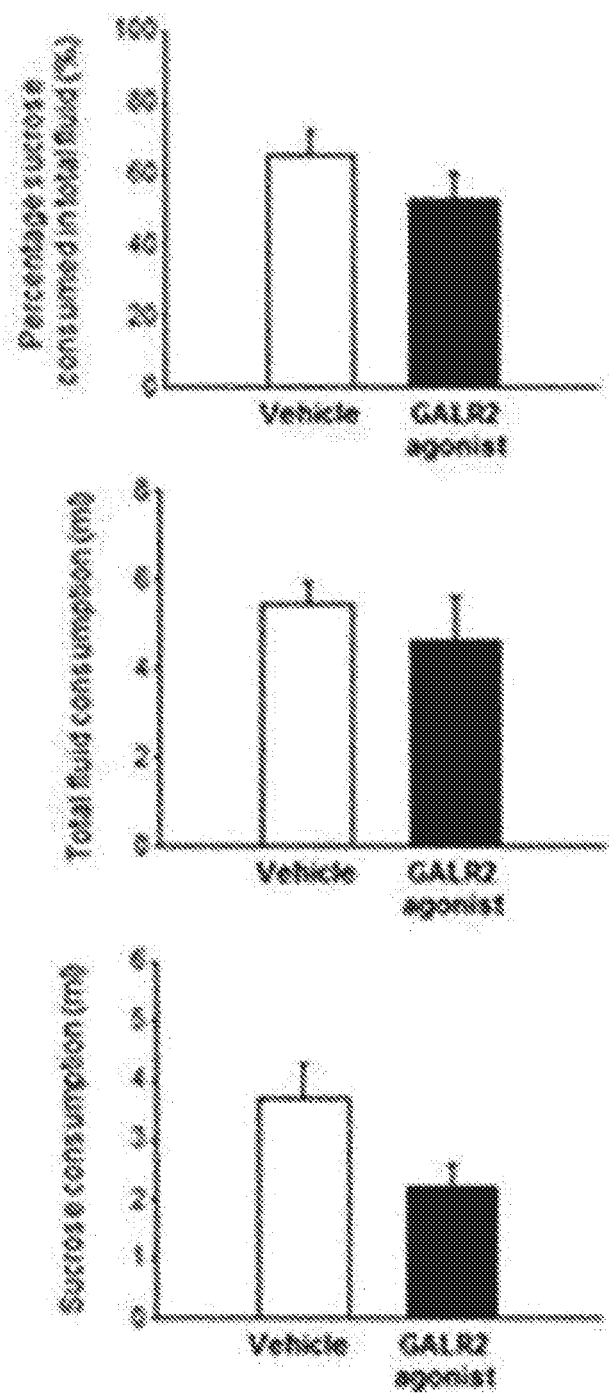
FIG. 16 shows effects of a GALR2 agonist on addiction reduction in animal models, which were investigated by measuring the percentage of sucrose consumed in total fluid (top), total fluid consumption (middle), and 1% sucrose consumption (bottom) for 2 days using the sucrose preference test (SPT).

Further, the effect of the GALR2 agonist on addiction reduction was investigated. To this end, a cannula was inserted into the lateral ventricle of animal models and the SPT was conducted to measure addiction. As a result, the sucrose consumption was considerably reduced, indicating reduced addiction to sweetness (FIG. 16). The reduced consumption of sucrose as an energy source can mean reduced appetite or feeding behaviors. Therefore, the GALR2 agonist can be used as a therapeutic agent for addiction and eating disorder.

In order for peptidergic drugs to be delivered to the body and act on the brain, drug delivery vehicles capable of penetrating the blood brain barrier (BBB) should be introduced. Drugs can be delivered intracerebrally via nasal inhalation without the need to develop small molecules penetrating the blood brain barrier.

Figure 17:
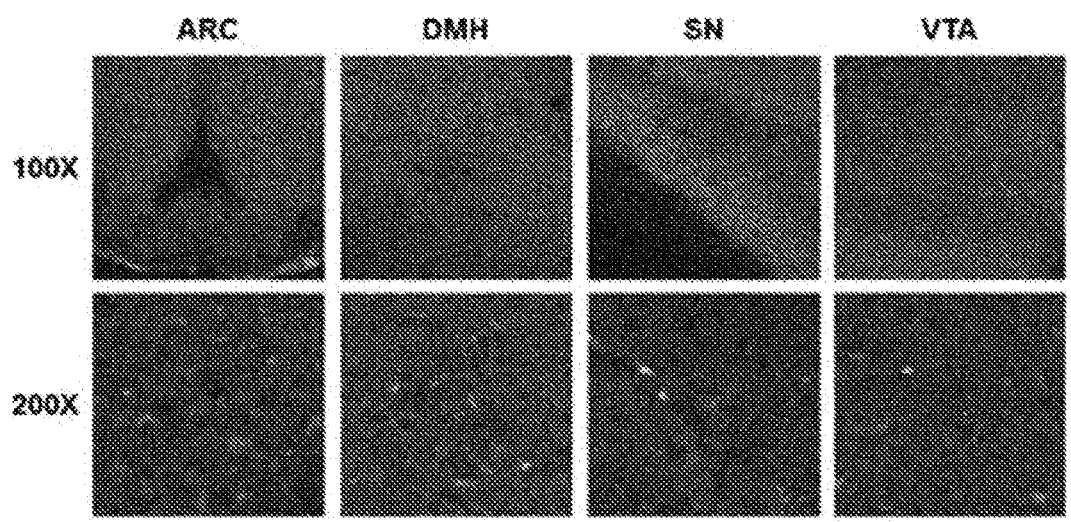
FIG. 17 shows immunohistochemistry (IHC) results of FITC-spexin delivered to the brain tissues of mouse models via nasal inhalation.
Figure 18:
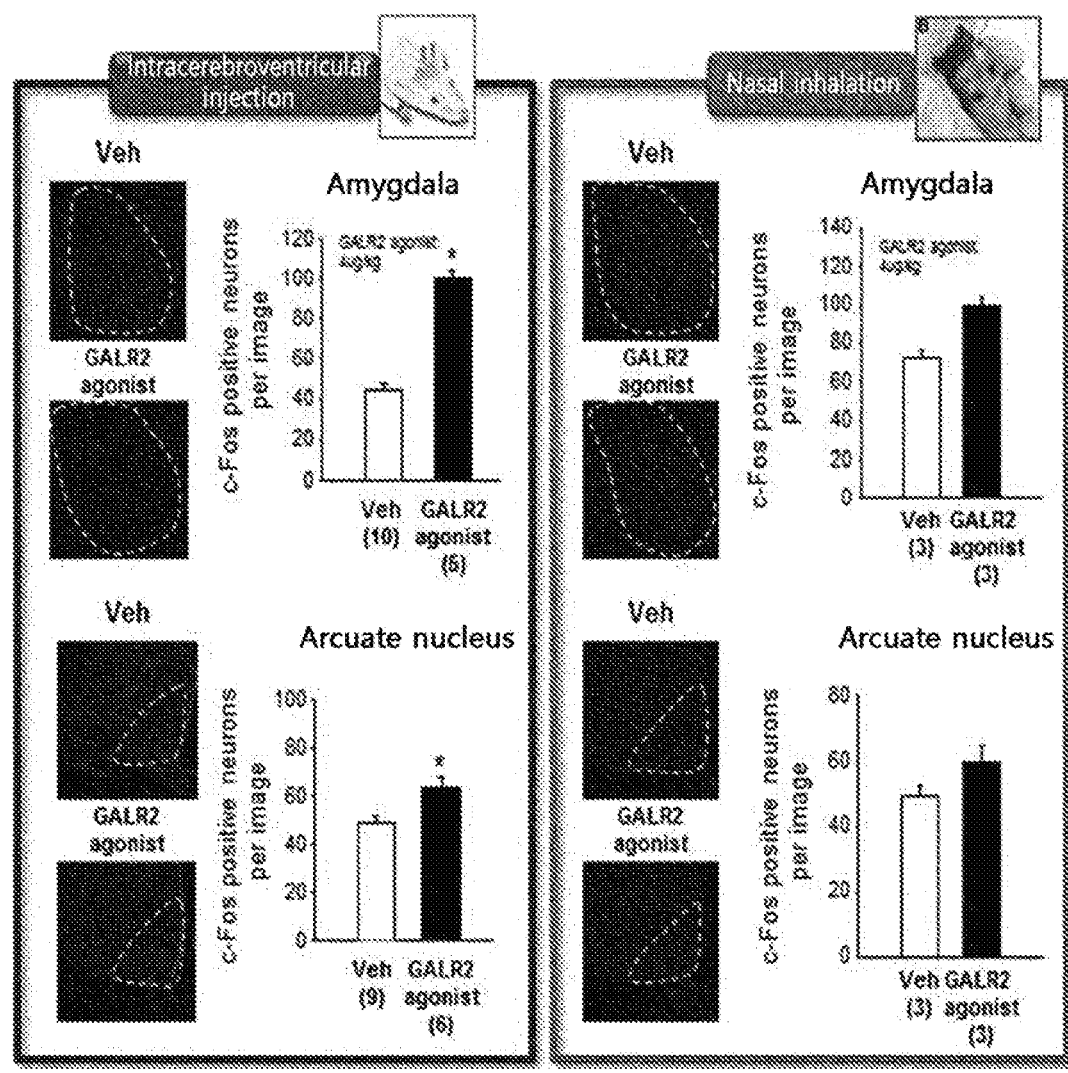
FIG. 18 shows increases in the activity of neurons in the amygdala and arcuate nucleus when a GALR agonist was delivered via nasal inhalation as an effective delivery route.

For nasal inhalation of spexin, fluorescent spexin was combined with propylene glycol and administered to the nose of animal models. As a result, punctates were found in the arcuate nucleus (ARC) region known to regulate appetite and the substantia nigra-ventral tegmental area (SN-VTA) known to be involved in emotion regulation (FIG. 17). The nasal inhalation was observed to induce the activity of neurons in the amygdala and arcuate nucleus, like ventricular injection in the two brain regions (FIG. 18). This suggests that nasal inhalation can be used for intracerebral delivery of peptidergic drugs and the GALR2 agonist prepared by amino acid substitution of spexin can be developed as a therapeutic agent for eating- and emotion-related diseases.

The GALR2 agonist of the present invention can be synthesized by a suitable method known in the art, including chemical synthesis (W. H. Freeman and Co., Proteins; structures and molecular principles, 1983). Specific examples of such methods include, but are not limited to, solution phase peptide synthesis, solid-phase peptide synthesis, fragment condensation, and F-moc or T-BOC chemistry.

The GALR2 agonist of the present invention can be prepared by a gene engineering technique. First, a DNA sequence encoding the peptide is constructed according to a conventional method. The DNA sequence may be constructed by PCR amplification using appropriate primers. Alternatively, the DNA sequence may also be synthesized using a standard apparatus known in the art, for example, an automated DNA synthesizer (commercially available from Biosearch or Applied Iosystems). Then, the constructed DNA sequence is inserted into a vector including one or more expression control sequences (for example, promotors and enhancers) which are operatively linked to the DNA sequence. Not that the expression control sequences regulate the expression of the DNA sequence. A host cell is then transformed with the resulting recombinant expression vector. The resulting transformants are cultured under a medium and culture conditions suitable to induce the expression of the DNA sequence. Then, a substantially pure peptide encoded by the DNA sequence is recovered from the cell culture. The recovery of peptide can be carried out by a conventional method known in the art (for example, chromatography). As used herein, the term "substantially pure peptide" means that the peptide of the present invention is substantially free from any other proteins derived from the host. The genetic engineering method for synthesis of the peptide of the present invention can be found in the following literature: Maniatis et al., Molecular Cloning; A laboratory Manual, Cold Spring Harbor laboratory, 1982; Sambrook et al., Molecular Cloning: A Laboratory Manual, ColdSpring Harbor Press, N.Y., Second (1998) and Third (2000) Edition; Gene Expression Technology, Method in Enzymology, Genetics and Molecular Biology, Method in Enzymology, Guthrie & Fink (eds.), Academic Press, San Diego, Calif., 1991; and Hitzeman et al., J. Biol. Chem., 255:12073-12080, 1990.

The present invention also provides a composition for preventing or treating a galanin receptor type 2-mediated disease including the peptide-based galanin receptor type 2 agonist.

The galanin receptor type 2-mediated disease may be attention deficit hyperactivity disorder (ADHD), bipolar disorder, body dysmorphic disorder, bulimia nervosa and other eating disorders, cataplexy, dysthymia, general anxiety disorder, hypersexuality, irritable bowel syndrome, impulse-control disorder (MDD), kleptomania, migraine, major depressive disorder, narcolepsy, obsessive-compulsive disorder, oppositional-defiant disorder, panic disorder, post-traumatic stress disorder (PTSD), premenstrual dysphoric disorder (PMDD), social anxiety disorder, chronic pain, intermittent explosive disorder, pathological gambling, personality disorder, pyromania, substance abuse and addiction, trichotillomania or Alzheimer's disease. Preferably, the GALR2 agonist of the present invention is used to prevent or treat bulimia nervosa, eating disorder, obesity disorder, general anxiety disorder, post-traumatic stress disorder. obsessive-compulsive disorder, panic disorder, social anxiety disorder, substance abuse and addiction or Alzheimer's disease.

The pharmaceutical composition of the present invention may further include a pharmaceutically acceptable carrier.

Suitable pharmaceutically acceptable carriers include carriers and vehicles commonly used in the art. Specific examples of pharmaceutically acceptable carriers include, but are not limited to, ion exchange resins, alumina, aluminum stearate, lecithin, serum proteins (e.g., human serum albumin), buffer substances (e.g., various phosphates, glycine, sorbic acid, potassium sorbate, and partial glyceride mixtures of saturated vegetable fatty acids), water, salts or electrolytes (e.g., protamine sulfate, disodium hydrogen phosphate, potassium hydrogen phosphate, sodium chloride, and zinc salts), colloidal silica, magnesium trisilicate, polyvinyl pyrrolidone, cellulose-based substances, polyethylene glycol, sodium carboxymethylcellulose, polyarylates, waxes, polyethylene glycol, and wool fat.

The composition of the present invention may further include a lubricating agent, a wetting agent, an emulsifying agent, a suspending agent or a preservative.

In one embodiment, the composition of the present invention may be prepared into an aqueous solution for parenteral administration, preferably a buffer such as Hank's solution, Ringer's solution or physiologically buffered saline. Aqueous injection suspensions may contain substances that increases the viscosity of the suspensions, such as sodium carboxymethyl cellulose, sorbitol or dextran.

The composition of the present invention may be administered systemically or locally. For such administration, the composition may be prepared into appropriate formulations by techniques known in the art. For example, the composition for oral administration may be mixed with an inert diluent or an edible carrier, sealed in a hard or soft gelatin capsule, or compressed into tablets. The active compound may be mixed with a suitable excipient and used in the form of ingestible tablets, buccal tablets, troches, elixirs, suspensions, syrups, and wafers for oral administration.

For injection or parenteral administration, the composition may be prepared into an injectable freeze-dried powder or solution by a suitable technique known or commonly used in the art. The GALR2 agonist is freeze-dried and stored before use due to its high solubility in saline or buffer. Just before administration, an effective amount of the GALR2 agonist is dissolved in saline or buffer to prepare a solution suitable for intravenous administration, subcutaneous administration, intramuscular administration, intraperitoneal administration or transdermal administration. More preferably, the composition is prepared into a formulation for intranasal administration for brain delivery.

The effective amount of the active ingredient of the pharmaceutical composition according to the present invention refers to an amount required to prevent, prevent or ameliorate the intended disease.

Accordingly, the effective amount will depend on a variety of factors, including the kind and severity of the disease being treated, the kinds and contents of the active ingredient and other ingredients of the composition, the type of the formulation, the age, body weight, general health, sex, and diet of the patient, the time and route of administration, the rate of secretion of the composition, the duration of treatment, and combination with others drugs.

The dose and administration frequency of the active ingredient are not limited. For example, the active ingredient may be administered in an amount of 0.01 to 100 mg/kg, preferably 0.1 to 10 mg/kg for an adult. The active ingredient may be administered one to three times daily.

The present invention also provides a method for preventing or treating a galanin receptor type 2-mediated disease including administering a pharmaceutically effective amount of the composition to a subject in need of such prevention or treatment.

The pharmaceutical composition used in the method for treating a galanin receptor type 2-mediated disease and its mode of administration have been described above and a description thereof is omitted to avoid complexity.

According to the method of the present invention, the composition may be administered to any subject in need of such prevention or treatment.

Subjects to which the pharmaceutical composition can be administered include all animals, for example, humans, pigs, gorillas, monkeys, dogs, cats, mice, and other mammals.

The kind of the galanin receptor type 2-mediated disease is the same as that described above.

MODE FOR CARRYING OUT THE INVENTION

The advantages and features of the present invention and methods for achieving them will become more apparent from the following embodiments that are described in detail below. However, the present invention is not limited to the illustrated embodiments and may be embodied in various different forms. Rather, the disclosed embodiments are provided so that the disclosure of the present invention will be thorough and complete, and will fully convey the scope of the invention to those skilled in the art to which the present invention pertains. The scope of the present invention is defined by the claims that follow.

Figure 2A:
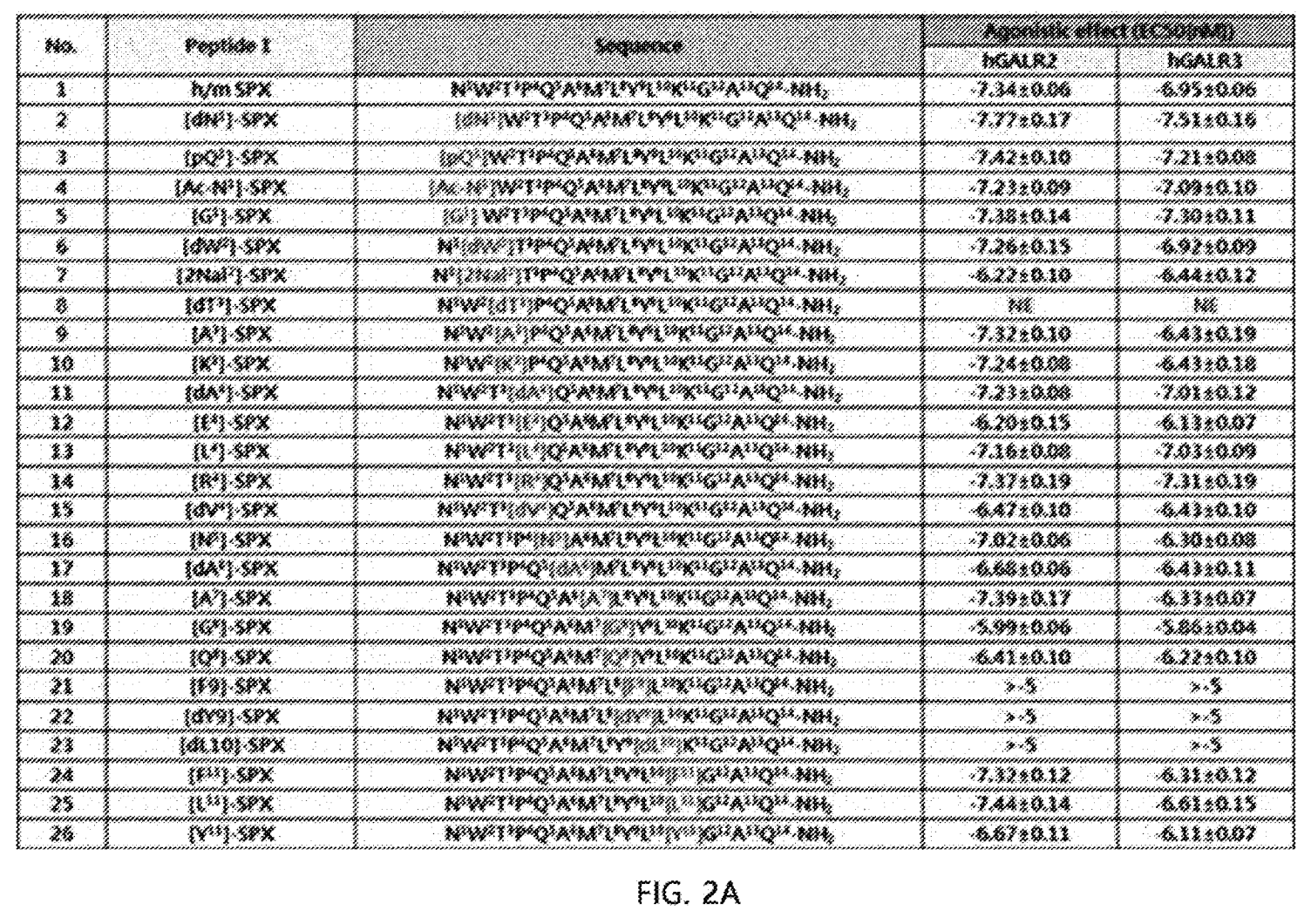
Figure 2B:
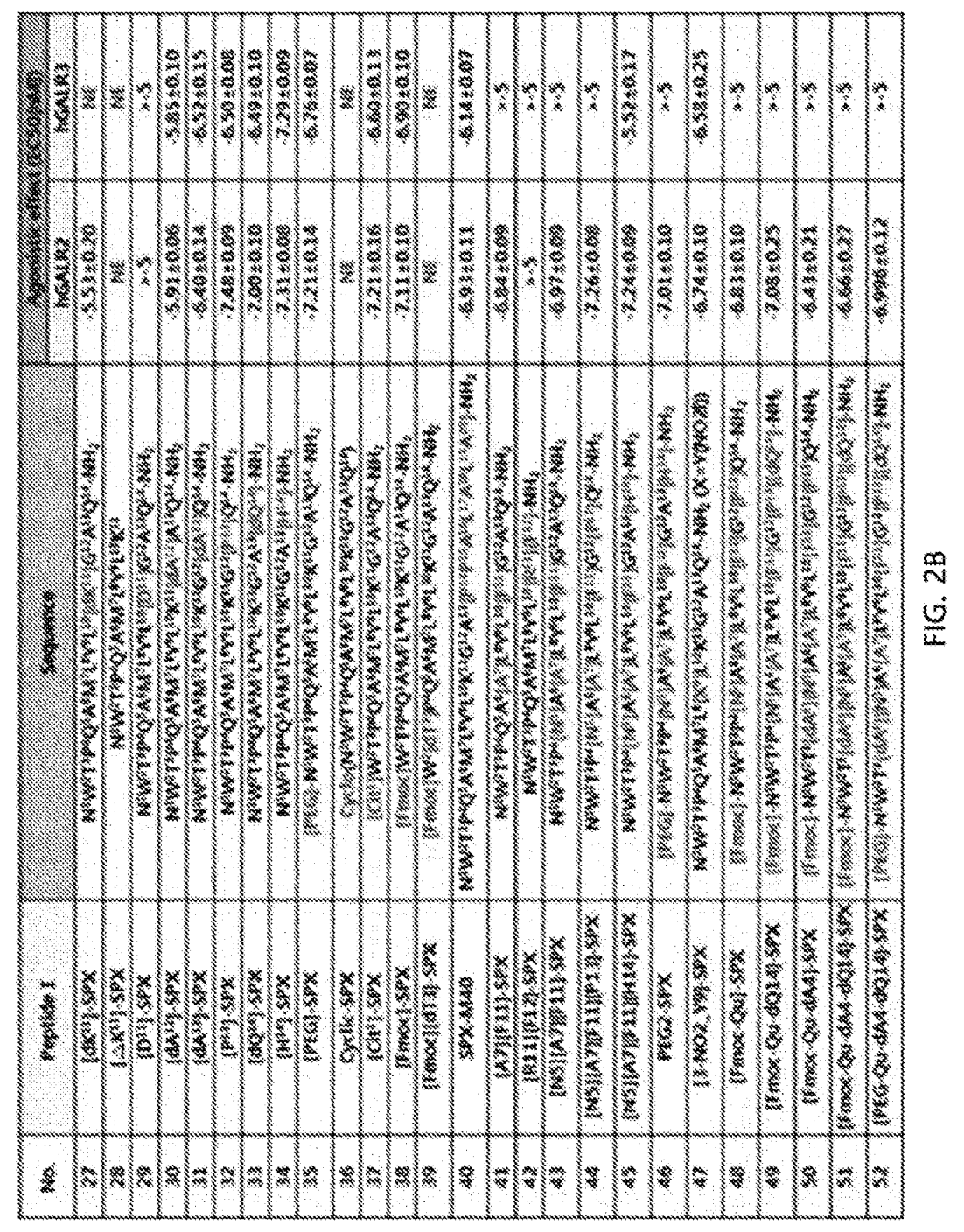

<Example 1> Development of GALR Type 2-Specific Stable Agonists by Amino Acid Substitution of Spexin The amino acid sequences of spexin1, spexin2, galanin, and galanin-like peptides were compared to develop agonists that selectively act on GALR2 and are long-acting. The amino acid sequences were downloaded from Ensembl (http://www.ensembl.org/index.html). Of these amino acid sequences, mature sequences were compared. Galanin and spexin present in various vertebrate species were confirmed to share tryptophan at position 2 [$Trp^2$], tyrosine at position 9 [$Tyr^9$], leucine at position 10 [Lee], and glycine at position 12 [$Gly''$] in common when their amino acid sequences were compared. Mutant peptides were prepared by replacing the same amino acids of spexin and galanin with the corresponding D-amino acids. Mutant peptides were prepared by replacing the specific amino acids of spexin with the corresponding amino acids of galanin. Mutant peptides were prepared by replacing the 14 amino acids of spexin with different amino acids or the corresponding D-amino acids. Changes in the activity of the mutant peptides on galanin receptors were observed (FIG. 1 and FIGS. 2A and 2B).

According to the previous literature, it is known that G protein-coupled receptors bound to agonists replace guanosine diphosphate (GDP) bound to the α-subunits of the G proteins with guanosine triphosphate (GTP) to induce intracellular signal transduction. G proteins are heterotrimers, each of which consists of α-, β-, and γ-subunits. The most important signals in intracellular signal transduction are generated from the α-subunit. The α-subunit may be of s-type (Gas), i-type (Gai) or q/11-type. The s-type α-subunit activates adenyl cyclase as an intracellular enzyme to produce cAMP, the universal second messenger, from adenosine triphosphate (ATP) and activates protein kinase A (PKA). In contrast, the i-type α-subunit sends signals suppressing the activity of adenyl cyclase and the q/11-type α-subunit increases the intracellular level of calcium or activates protein kinase C (PKC). Binding between G protein-coupled receptors and G proteins is a unique characteristic depending on the receptor type. GALR subtypes 1 and 3 induce inhibitory G-coupled signaling, while GALR subtype 2 triggers stimulatory $G_q$-coupled signaling. This difference explains the use of the HEK293-$G_{qi}$ stable cell line in which the C-terminus of $G_q$ is substituted with 3 amino acids of G to convert the signals of G to $G_q$ signaling pathways. The activities of the receptors were measured using an SRE-luc assay system designed to express luciferase (luc) by serum responsive element (SRE) promoters. Light caused by a reaction between expressed luciferase and luciferin as a substrate was detected using a luminometer so that receptor subtype-specific or ligand-specific cellular activities were observed. One day after HEK293-$G_{qi}$ cells were seeded in 48-well plates at a density of $2 \times 10^4$ cells/well, plasmid DNA and SRE-luc plasmid DNA, which encode GALR2 and GALR3, respectively, were mixed in a ratio of 1:1 (75 ng+75 ng)/well, and treated with Effectene reagent (2 μl/well). After 3 h, media were replaced with DMEM media supplemented with 10% FBS. After 24 h, the DMEM media were replaced with FBS-free DMEM media. After 16 h, each constructed spexin-based mutant peptide was further incubated at 37° C. for 6 h. After this stage was finished, cells were washed with PBS and lysed by the addition of 100 µl of lysis buffer (0.1% triton X-100, 0.2M Tris, pH 8.0) at room temperature for 20 min. The luciferase activity was determined using a synergy 2 Multi-mode microplate reader (BioTek, Winooski, Vt., USA) with automatic injection of a luciferin solution (0.5 M MgCl$_2$, 0.1 M ATP, 0.05 M D-luciferin, 1 M KH$_2$PO$_4$, pH 7.8).

As shown in FIGS. 3A to 3D and FIG. 4, the mutant peptide in which leucine at position 8 of spexin was replaced with glycine [Gly$^8$] showed decreased potencies toward both GALR2 and GALR3. The mutant peptide in which asparagine at position 1 of spexin was replaced with glycine [Gly'], the mutant peptide in which leucine at position 4 of spexin was replaced with leucine [Leu$^4$], and the mutant peptide in which glutamine at position 11 of spexin was replaced with histidine [His$^{14}$] maintained their potencies toward both receptors without differences from those of spexin. The mutant peptide in which glutamine, methionine, lysine, and alanine at positions 5, 7, 11, and 13 were replaced with asparagine [Asn$^5$], alanine leucine [Leu$^{11}$] or phenylalanine [Phe$^{11}$], and proline [Pro$^{13}$] maintained its potency toward GALR2 without a substantial difference but a decreased potency toward GALR3. These results suggest that glutamine at position 5 [Gln$^5$], methionine at position 7 [Met$^7$], lysine at position 11 [Lys$^{11}$], and alanine at position 13 [Ala$^{13}$] of the spexin amino acid sequence are important residues in activating GALR3 rather than GALR2. For additional investigation, multiple mutants were constructed in which the amino acids at positions 5, 7, 11, and 13 of the spexin sequence were replaced with the corresponding amino acids of the galanin sequence. The potencies of the double mutant (A$^7$F$^{11}$) in which the amino acids at positions 7 and 11 were replaced with alanine [Ala$^7$] and phenylalanine [Phe$^{11}$], respectively, and the triple mutant (N$^5$A$^7$F$^{11}$) in which the amino acid at positions 5, 7, and 11 were replaced with asparagine [Asn$^5$], alanine [Ala$^7$], and phenylalanine [Phe$^{11}$], respectively, toward GALR3 were considerably reduced. Particularly, the double and triple mutants could maximally activate GALR3 at a high concentration of 10 µM. The quadruple mutant (N$^5$A$^7$F$^{11}$P$^{13}$ or Qu) in which the amino acids at position 5, 7, 11, and 13 (alanine) were replaced with asparagine [Asn$^5$], alanine [Ala$^7$], phenylalanine [Phe$^{11}$], and proline [Pro$^{13}$], respectively, maintained its potency toward GALR2 at a level comparable to that of spexin but lost its potency toward GALR3 (FIGS. 3A to 3D and FIG. 4). The introduction of the amino acids of galanin into spexin did not induce the potency toward GALR1, indicating specificity of the corresponding amino acids for the activation of GALR2.

The purpose of D-amino acid substitution is to identify important residues that are responsible for receptor activation and to determine residues that are tolerant of D-amino acid substitution, which functions to protect the peptide from attacks by a large variety of proteases present in serum. Cells expressing GALR2 or GALR3 were treated with the mutants in which the amino acids of spexin were replaced with the corresponding D-amino acids to measure the activities of the mutants (FIGS. 5A and 5B and FIG. 6). Of these mutants, the mutant in which the amino acids at positions 3, 9, and 10 were replaced with the corresponding D-amino acids exhibited a drastic loss of activity toward both GALR2 and GALR3, suggesting that the amino acids at positions 3, 9, and 10 of spexin may play a critical role in the activation of both receptors. The moderate loss of activity toward both receptors was observed for the mutant in which the amino acids at positions 6, 12, and 14 were replaced with the corresponding D-amino acids. The substitutions of the amino acids at positions 2 and 4 only slightly affected the activation of both receptors, suggesting that tryptophan at position 2 [Trp$^2$] and alanine at position 4 [Ala$^4$] are not crucial for activation of GALR2 and GALR3. The substitution of asparagine at position 1 [Asn$^1$] of spexin with the corresponding D-amino acid [dN$^1$] slightly increased the potency toward both GALR2 and GALR3 (FIGS. 5A and 5B and FIG. 6). Such changes show that the substitution of the amino acid at position 1 of spexin affords the possibility of developing stable agonists against proteases in serum. Thus, asparagine at position 1 [Asn$^1$] of spexin was replaced with pyroglutamate (pQ), citrulline (Cit), Fmoc, etc. or the N-terminus of spexin was polyethylene glycosylated (PEG) or acetylated. Such modifications had no influence on the potencies toward GALR2 and GALR3, similarly to the D-amino acid substitutions (FIGS. 5A, 5B, and 6). This strongly suggests that the substitution of the amino acid at position 1 of spexin increases the stability against proteases in serum while having no influence on the potency toward GALR.

<Example 2> Investigation of Stability of the GALR2 Agonists in 100% Fetal Bovine Serum The stability of the spexin-based mutant peptides was investigated. To this end, first, each modified mutant peptide at an initial concentration 10 µM was allowed to react in 100% fetal bovine serum (FBS) at 37° C. for 0, 3, 6, 12, 24, 48, and 72 h. Thereafter, the potencies of the mutant peptide toward GALR2 were determined via inositol 1,4,5-triphosphate (IP3) production in GALR2-expressing cells. For the IP3 assay, cells were seeded in 12-well plates at a density of 2.5×10$^5$ cells/well and then the next day, cells were treated with a mixture of 1 µg of GALR2-encoding plasmid DNA and Lipofectamine 2000 (Invitrogen). On day following treatment, cells were incubated in M199 media containing 1% FBS, 1% L-glutamine, 1% antibiotic, and myo-$^3$H inositol 1 µCi/well for 20 h to radioactively label inositol phosphate. After this stage was finished, cells were allowed to react in buffer A (140 mM NaCl, 20 mM Hepes, 4 mM KCl, 8 mM D-glucose, 1 mM MgCl$_2$, 1 mM CaCl$_2$), 1 mg/ml free fatty acid bovine serum albumin, and 10 mM LiCl at pH 7.2) for 30 min. After the mutant peptide was allowed to react in 100% FBS, cells were treated with the mutant peptide for 40 min at 37° C. Media was removed, and reactions were terminated by addition of 1 ml of 10 mM cold formic acid to each well. The plates were allowed to stand at 4° C. for 30 min. Then, the resulting extracts were transferred to 6-mL plastic tubes containing 500 µl AG1-8X anion exchange columns. The tubes were gently mixed with a vortexer, and the supernatants were removed from the labeled mixture. Two washes with 1 ml of triple-distilled water were performed followed by two additional washes with 60 mM ammonium formate/5 mM sodium tetraborate. The radioactively labeled mixture was eluted from the column with 1 ml of 1 M ammonium formate/0.1 M formic acid (1 mL), and 800 µl from the elution were taken from each tube and transferred into scintillation vials. Then, 2 ml of scintillation cocktail solution (Ultima Gold™, Perkin Elmer, Waltham Mass., USA) was added to each sample. The radioactivity of the mixture solution of the radioactively labeled mixture and the scintillation cocktail solution was measured using a TRI carb 2100TR liquid scintillation analyzer (Packard).

As shown in FIGS. 7A to 7E and FIG. 8, the potency of spexin was very rapidly reduced to 80% or less within 12 h but the mutant peptide (dAla4) in which alanine at position 4 was substituted and the N-terminus was modified underwent less reduction in IP3 production than the wild-type spexin, indicating its better stability (FIG. 7A). These results imply that the substitution of the N-terminus of spexin with hydrophobic molecules, such as PEG or Fmoc molecules, or the replacement of alanine at position 4 and glutamine at position 14 with the corresponding D-amino acids increased the stability of the peptide in serum.

Meanwhile, the dAla4 and dGln14 substitutions extended the life of the peptides in serum.

Figure 7B:
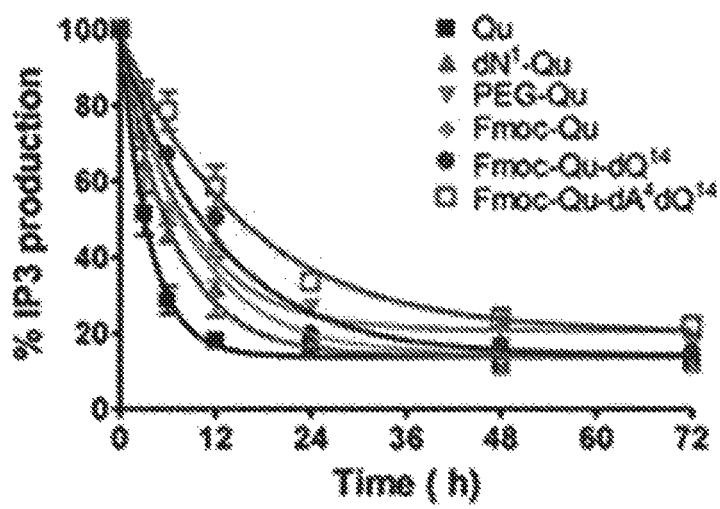
FIG. 7B shows stabilities of spexin-based quadruple mutant peptides (Qu analogs) in the presence of 100% PBS.
Figure 7C:
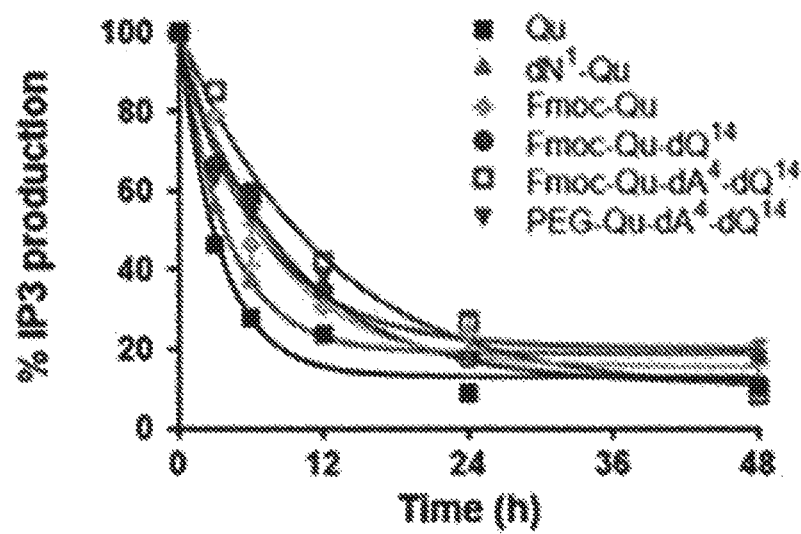
FIG. 7C shows stabilities of spexin-based quadruple mutant peptides (Qu analogs) in human serum.

Further, the quadruple mutant (Qu), the mutant peptides in which the N-terminus of the quadruple mutant was modified and/or the mutant peptide in which the amino acids at positions 4 and 14 were replaced with the corresponding D-amino acids, were measured for their degradation in serum. The quadruple mutants were rapidly degraded compared to the wild-type spexin but the mutant peptides having undergone N-terminus substitution with FEG or Fmoc and the mutant peptide having undergone double substitution of the amino acids at positions 4 and 14 had extended lifetimes in FBS and human serum, indicating their increased stability (FIGS. 7B and 7C).

Figure 7D:
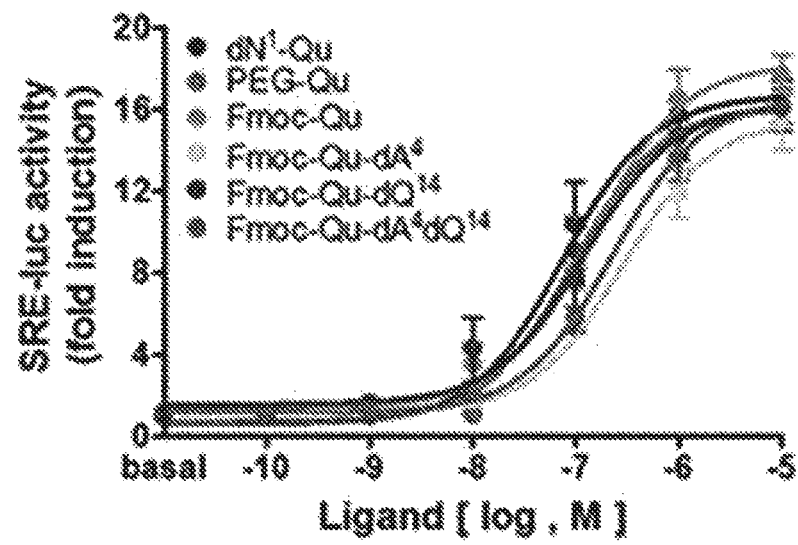
FIG. 7D shows the potencies of spexin-based quadruple mutant peptide analogs toward a galanin receptor in the HEK293-$G_{qi}$ stable cell line expressing GALR2.
Figure 7E:
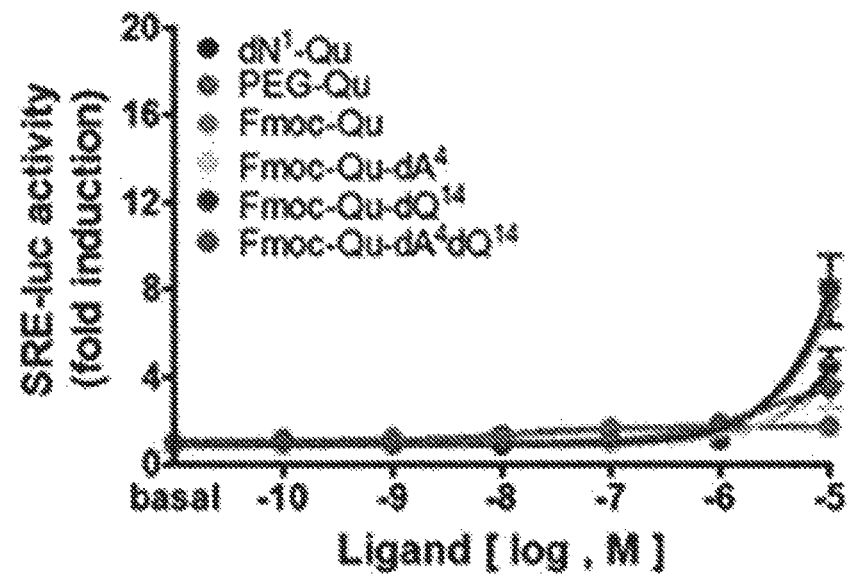
FIG. 7E shows potencies of spexin-based quadruple mutant peptide analogs toward a galanin receptor in the HEK293-$G_{qi}$ stable cell line expressing GALR3.
Figures 8, 9A:
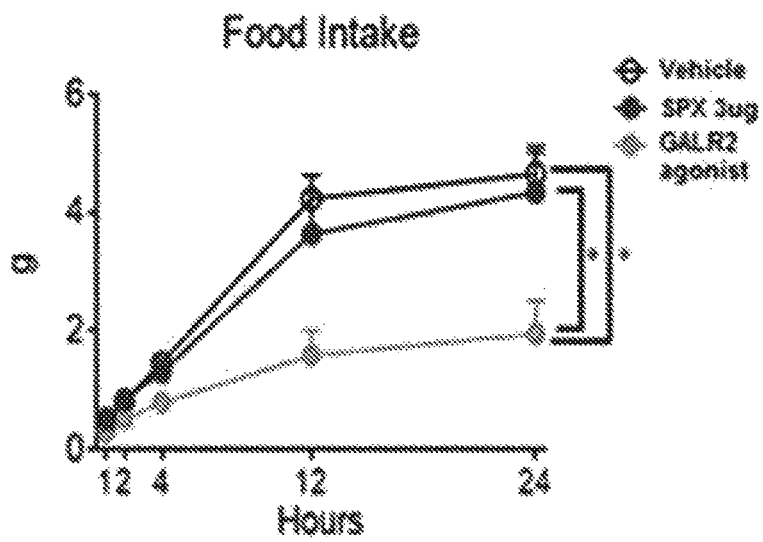
FIG. 8 shows quantified stabilities of spexin-based mutant peptides in 100% FBS and human serum.
FIG. 9A shows regulatory effects of a GALR2 agonist and spexin on feeding behaviors.

The N-terminus modified quadruple mutant peptides showed potencies toward GALR2 and GALR3 at a level similar to the quadruple mutants (FIGS. 7D and 7E and FIG. 8). The potencies of the modified quadruple mutant peptides toward GALR3 were observed only at a high concentration (10 μM). These results conclude that the mutant peptides presented in FIG. 8 are improved GALR2 agonists that specifically act on GALR2 at levels similar to the quadruple mutants of spexin and are maintained very stable in serum.

<Example 3> Investigation of Inhibitory Effect of the GALR2 Agonists on Food Intake C57BL/6J black male mice (9 weeks of age) were acquired from Orientbio (www.orient.co.kr). Mice were housed in a cage at 20-24° C. and 40-70% relative humidity under a normal 12:12 light-dark cycle (lights onset at 8:00 am), with food and water available ad libitum. All experiments were designed to minimize the number of animals. Animals were anesthetized to minimize their suffering in accordance with the Guidelines for Ethical Care and Use of Experimental Animals, which were approved by the institutional animal care and use committee of Korea University. For intracerebroventricular injection, mice were anesthetized with sodium pentobarbital (50 mg/kg, i.p.), mounted on a stereotaxic apparatus, and implanted with a 26-gauge stainless steel cannula into the right side of the lateral ventricle. Two jewelry screws were implanted into the skull as anchors, and the whole assembly was affixed to the skull with dental cement. Mice were recovered at least 2 weeks before experimentation. The GALR2 agonist was administered using a Hamilton syringe at a rate of 0.5 μl/min. Dietary intakes and weight changes were determined by measuring the weights of feed and mice before agonist administration, measuring the weights of the feed over 1, 2, 4, 12, and 24 h, and comparing the weight of mice after 24 h with the initial weight.

Figure 9B:
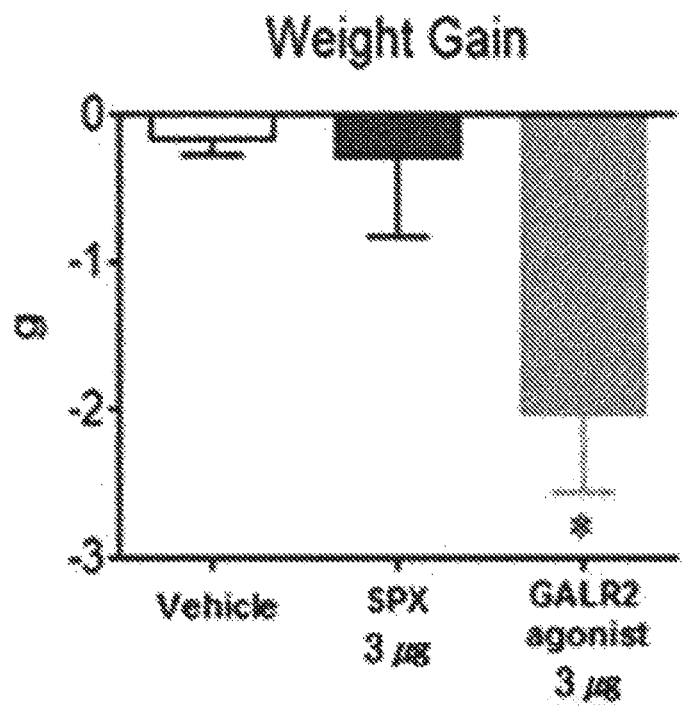
FIG. 9B shows regulatory effects of a GALR2 agonist and spexin on changes in body weight.
Figure 9C:
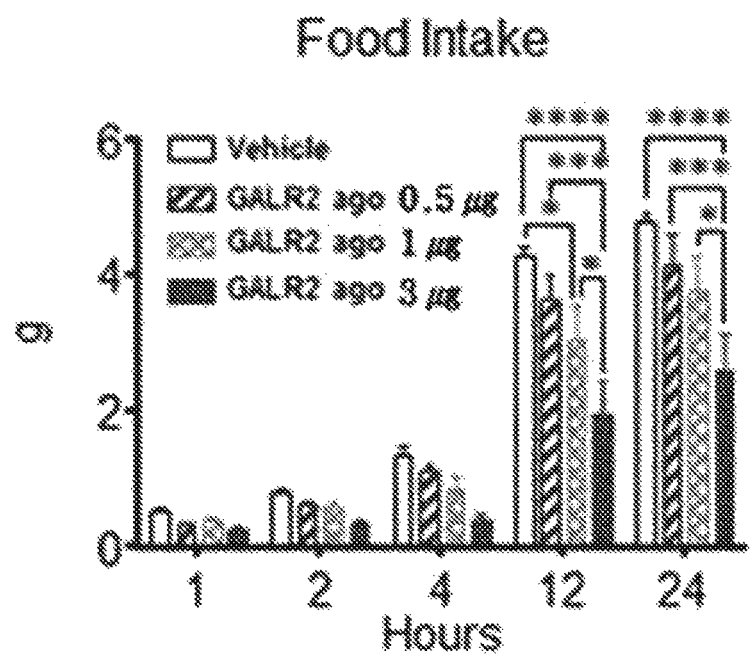
FIG. 9C shows regulatory effects of different concentrations of a GALR2 agonist on feeding behaviors.
Figure 9D:
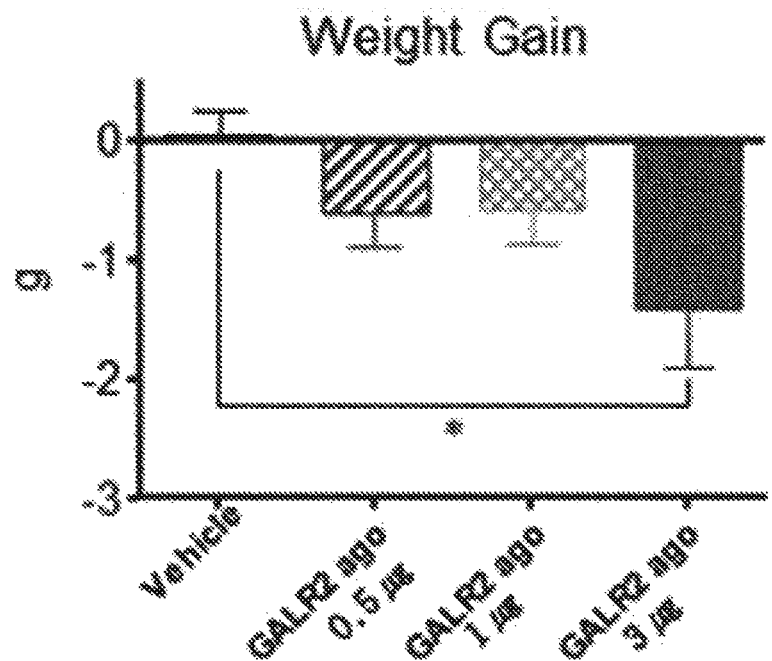
FIG. 9D shows regulatory effects of different concentrations of a GALR2 agonist on changes in body weight.
Figure 9E:
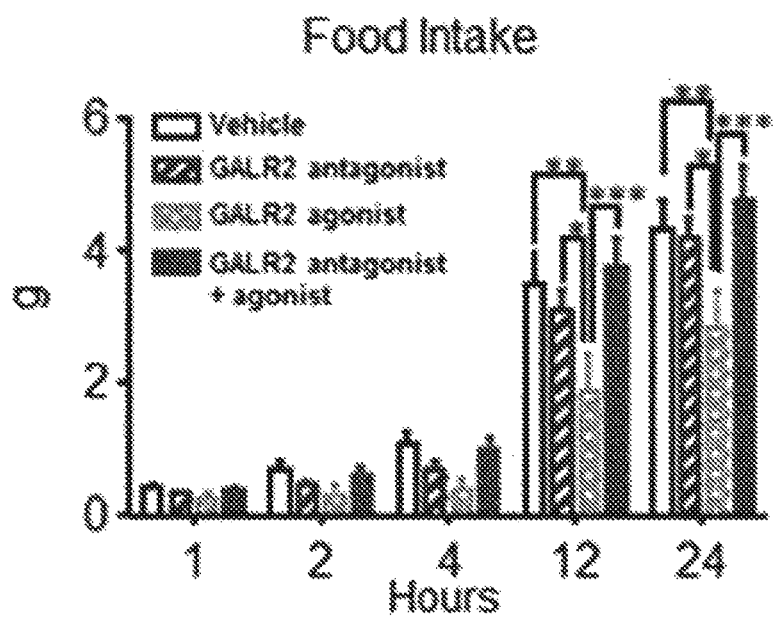
FIG. 9E shows regulatory effects of a GALR2 agonist and a GALR2 antagonist on feeding behaviors.
Figure 9F:
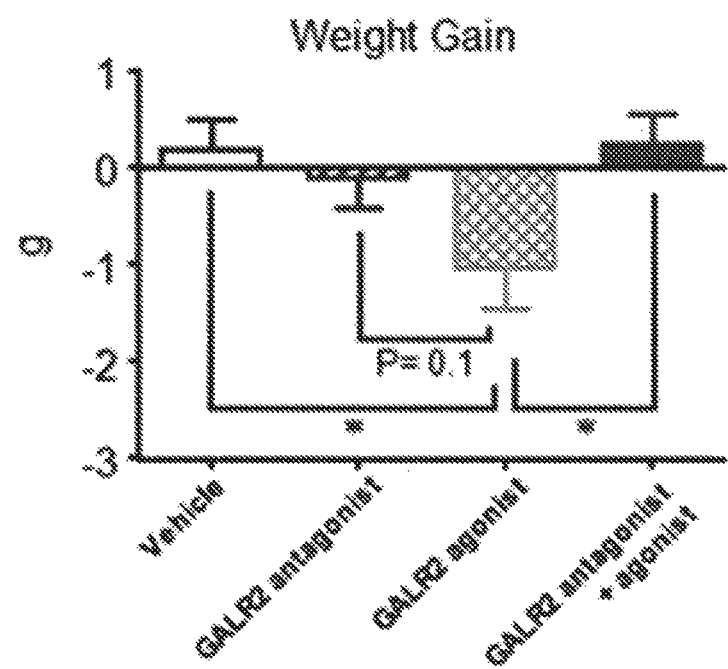
FIG. 9F shows regulatory effects of a GALR2 agonist and a GALR2 antagonist on changes in body weight.

The effects of the GALR2 agonist on feeding behaviors and changes in body weight were investigated by the following procedure. First, a cannula was inserted into the third ventricle. After administration of 3 μg of artificial cerebrospinal fluid (acsf) as a control or 3 μg of spexin as an experimental group and 3 μg of the peptide dN1-Qu with increased stability in which the amino acid at position 1 of the quadruple mutant was replaced with the corresponding D-amino acid, changes in the body weight and dietary intake of the animals for 24 h were compared. The dietary intake was significantly decreased and a weight loss was effectively induced with the passage of time in the mice administered the GALR2 agonist compared to the spexin-administered mice and the control (FIGS. 9A and 9B). After the PEG sextuple mutant were administered at concentrations of 0.5, 1, and 3 dietary intakes and weight losses were observed (FIGS. 9C and 9D). When 3 μg of the PEG sextuple mutant were administered following the administration of 10 μg of M871, the effects of the PEG sextuple mutant on dietary intake and weight loss disappeared (FIGS. 9E and 9F).

An increase in the potency of appetite-regulating brain neurons by administration of the GALR2 agonist was determined by immunohistochemistry (IHC). 1 h after 0.4, 4, and 40 μg of the GALR2 agonist dN1-Qu were administered to the ventricle of adult mice, the animals were intraperitoneally injected for anesthesia, the chest was cut, a Ringer needle was inserted into the left cardiac ventricle to drain blood with 0.9% physiological saline (50 mL), the cardiac ventricle was fixed with 0.9% phosphate buffered saline (200 mL) containing 4% paraformaldehyde for 24 h, and the brain was treated with phosphate buffered saline containing 30% sucrose solution for ~24 h. Then, the brain was placed in a mold for brain tissue, transferred to and frozen in an isopentane solution kept cold on dry ice with an OCT composite containing 30% sucrose solution, and stored at −80° C. before use. The frozen brain tissue was sliced at 40 μm using a cryostat microtome, followed by immunohistochemistry. The d-fos antibody suitable for identifying the activity of neurons (1:2000 dilution ratio) was used to investigate an increase in the number of c-fos expressing neurons in the arcuate nucleus, an appetite-regulating brain region, when the GALR2 agonist was administered (FIG. 10). POMC neurons known to regulate appetite in the arcuate nucleus were cultured in vitro, treated with the Fmoc sextuple mutant (1 μM) and 10 nM insulin, washed with PBS, and lysed by the addition of 100 μl of lysis buffer (0.1% triton X-100, 0.2M Tris, pH 8.0) at room temperature for 20 min.

Proteins were extracted from cells and analyzed by Western blotting. AKT and ERK were phosphorylated by insulin but only the ERK pathway was phosphorylated by the GALR2 agonist, indicating that GALR2 acts through a pathway different from insulin (FIG. 11A). POMC neurons were treated the GALR2 agonist and mRNA was then extracted. Increases in the number of the POMC neurons and the level of α-MSH were observed (FIGS. 11B to 11E). This suggests that the improved GALR2 agonist can be used as a drug for obesity treatment due to its ability to suppress feeding behaviors.

<Example 4> Measurement of Efficacy of the Agonist dN1-Qu on Recovery from Anxiety Disorder The effect of the GALR2 agonist dN1-Qu on recovery from anxiety disorder was investigated. In the same manner as in Example 3, a cannula was inserted into the lateral ventricle of mice. 2-3 h after dimethyl sulfoxide (DMSO) as a control or 4 μg of the GALR2 agonist dN1-Qu as an experimental group was administered, the elevated plus maze (EPM) test was conducted to measure anxiety/obsession. The EPM test uses a cross-shaped maze elevated above the floor with closed arms, open arms, and a center and is based on the behavior of mice that prefer to remain in the closed arms. Anxiety is judged to be lower when a larger number of mice remain in the open arms. After mice was placed on the plus maze, the time spent in the open arms ("time in open arm"), the number of mice entering the open arms ("number of open arm entry"), and the total movement ("number of center crossing") were measured for the first 15 min. The results for the last 10 min were used for analysis.

Figure 12:
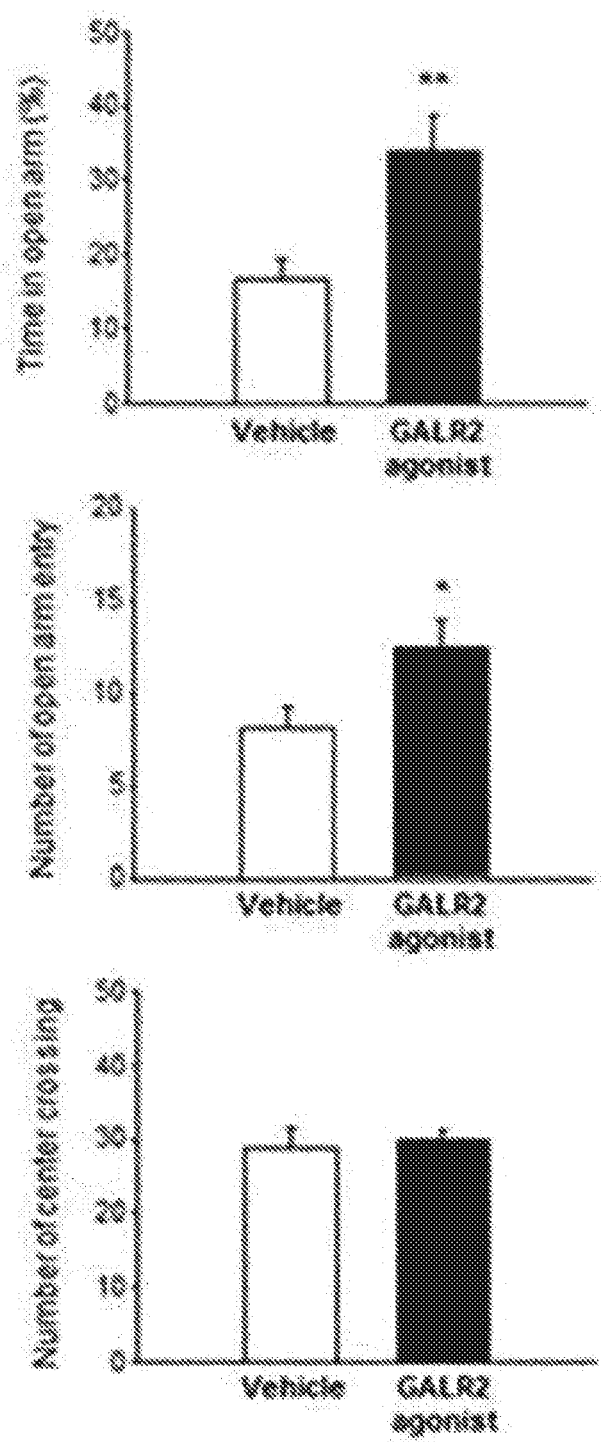
FIG. 12 shows the time in open arm (%, top), the number of open arm entry (middle), and number of center crossing (bottom) in a plus maze for animal models, which were measured by the EPM test to investigate the therapeutic effects of a GALR2 agonist on anxiety disorder in the animal models.

After the GALR2 agonist was administered, there was no difference in the number of center crossing, and the time in open arm and the number of open arm entry were increased, indicating reduced anxiety (FIG. 12).

The effect of the GALR2 agonist on anxiety reduction was investigated by the OFT for simultaneously measuring movement and anxiety (FIG. 13). The OFT is based on the behavior of mice that prefer to stay at the periphery rather than at the center of a quadrangular area. After mice were placed at the center of a quadrangular area, the proportion of the time spent in the center ("% time in center"), the proportion of the moving distance in the center ("% distance in center"), and the total moving distance ("total distance") were measured for 10 min from the time when the animals moved to the periphery. The results were divided into two equal periods (5 min each) for analysis. 2-3 h after 4 μg of DMSO as a control or the GALR2 agonist dN1-Qu was administered to the lateral ventricle of animals, which had previously been evoked by repeated electric shocks to induce anxiety, anxiety and movement were measured.

During the first 5-min period, there was no difference in the total distance of the anxiety-induced mice compared to the control DMSO but the % distance in center was increased by the administration of the GALR2 agonist dN1-Qu, demonstrating that the GALR2 agonist is effective in reducing anxiety. During the second 5-min period, the anxiety of the DMSO-administered anxiety-induced mice was increased whereas the anxiety of the dN1-Qu-administered mice was reduced, which was demonstrated from the increased % distance in center (FIGS. 13A and 13B).

An increase in the potency of anxiety-regulating brain neurons by administration of the GALR2 agonist was determined by immunohistochemistry ~1-2 h after 0.4, 4, and 40 μg of the GALR2 agonist were administered to the ventricle of adult mice, the animals were intraperitoneally injected for anesthesia, the chest was cut, a Ringer needle was inserted into the left cardiac ventricle to drain blood with 0.9% physiological saline (50 mL), the cardiac ventricle was fixed with 0.9% phosphate buffered saline (50 mL) containing 4% paraformaldehyde for 24 h, and the brain was treated with phosphate buffered saline containing 30% sucrose solution for ~24 h. Then, the brain was placed in a mold for brain tissue, transferred to and frozen in an isopentane solution kept cold on dry ice with an OCT composite containing 30% sucrose solution, and stored at −80° C. before use. The frozen brain tissue was sliced at 40 μm using a cryostat microtome, followed by immunohistochemistry.

The d-fos antibody suitable for identifying the activity of neurons (1:2000 dilution ratio) was used to investigate an increase in the number of c-fos expressing neurons in the amygdala, an anxiety-regulating brain region, when the GALR2 agonist was administered (FIG. 14). In contrast, neurons in other emotion-regulating brain regions were not activated, demonstrating the specific effect of the GALR2 agonist on anxiety regulation (FIGS. 15A to 15D). This suggests that the GALR2 agonist can be used as a drug for treating anxiety disorder. The amygdala is closely related to anxiety disorder and post-traumatic stress disorder (PTSD), suggesting that the GALR2 agonist can also be used as a drug for PTSD treatment.

<Example 5> Identification of Efficacy of the GALR2 Agonist dN1-Qu on Addiction Reduction The effect of the GALR2 agonist dN1-Qu on addiction reduction was investigated. In the same manner as in Example 3, a cannula was inserted into the lateral ventricle of mice. After injection of dimethyl sulfoxide (DMSO) and 0.4, 4, and 40 μg of dN1-Qu, the consumptions of water and 1% sucrose solution were measured for 2 days by the sucrose preference test (SPT) for addiction evaluation. According to this test, tap water and sucrose solution were filled in respective bottles and weighed before injection of the agonist. After free access to the fluids for 2 days, the bottles were weighed to compare the total consumption of the fluids and the percentage of the consumed sucrose solution in the total fluid consumption.

As a result, there was no difference in the total consumption of the fluids for 2 days. For the control, the consumed sucrose solution accounted for ~70% of the total fluid consumption. In contrast, when the GALR2 agonist dN1-Qu was administered, the sucrose preference was decreased to ≤60%. The administration of the GALR agonist dN1-Qu considerably reduced the consumption of sucrose (FIG. 16). These results indicate that addiction to the sweet ingredient was reduced by the administration of the GALR2 agonist dN1-Qu. The reduced consumption of sucrose as an energy source can mean a reduction in appetite or feeding behaviors, suggesting the use of the GALR2 agonist as a therapeutic agent for addiction and eating disorder.

<Example 6> Identification of Intracerebral Delivery Via Nasal Inhalation

In order for peptidergic drugs to be delivered to the body and act on the brain, drug delivery vehicles capable of penetrating the blood brain barrier (BBB) should be introduced. Drugs can be delivered intracerebrally via nasal inhalation without the need to develop small molecules penetrating the blood brain barrier. Indeed, nasal inhalation was identified as a suitable drug delivery route for oxytocin. Based on the fMRI result that oxytocin administration induced a change in human brain activity, nasal inhalation is expected to more efficiently increase the effects of peptidergic drugs on the brain. The intracerebral delivery of spexin was identified by the following procedure. First, spexin was labeled with FITC as a fluorescent tracer (FITC-spexin) and combined with propylene glycol, which is used to study drug delivery via nasal inhalation. 4 μg of the combination product was administered to the nose of mice anesthetized with sodium pentobarbital (50 mg/kg, i.p.). After 3 h, brain regions where FITC fluorescence signals were seen were examined by immunohistochemistry (IHC). Animals were intraperitoneally injected for anesthesia, the chest was cut, a Ringer needle was inserted into the left cardiac ventricle to drain blood with 0.9% physiological saline (50 mL), the cardiac ventricle was fixed with 0.9% phosphate buffered saline (200 mL) containing 4% paraformaldehyde for 24 h, and the brain was treated with phosphate buffered saline containing 30% sucrose solution for ~24 h. Then, the brain was placed in a mold for brain tissue, transferred to and frozen in an isopentane solution kept cold on dry ice with an OCT composite containing 30% sucrose solution, and stored at −80° C. before use. The frozen brain tissue was sliced at 40 μm using a cryostat microtome, followed by immunohistochemistry.

As a result of nasal inhalation of the FITC-spexin, FITC fluorescence signals were found in the form of punctates in the arcuate nucleus (ARC) region known to regulate appetite and the substantia nigra-ventral tegmental area (SN-VTA) known to be involved in emotion regulation (FIG. 17). For nasal inhalation, the GALR2 agonist was combined with propylene glycol (PEG) and 8 μg of the PEG-se was administered to the nose. 1-2 h after nasal inhalation, the results were recorded. The results of nasal inhalation were compared with those of intracerebroventricular injection. The nasal inhalation of the GALR2 agonist was confirmed to increase the activity of neurons in the amygdala and arcuate nucleus, like the intracerebroventricular injection in the two brain regions (FIG. 18). This suggests that nasal inhalation can be used for intracerebral delivery of peptidergic drugs and the GALR2 agonist prepared by amino acid substitution of spexin can be developed as a therapeutic agent for eating- and emotion-related diseases.

INDUSTRIAL APPLICABILITY

The agonists of the present invention can be used to prevent or treat GALR2-mediated diseases.

The invention claimed is:

1. A peptide-based galanin receptor type 2 (GALR2) agonist having the amino acid sequence set forth in formula 1:

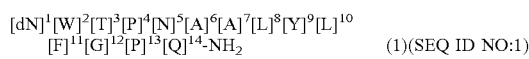
(1)(SEQ ID NO:1)

wherein, $[dN]^1$ is D-asparagine (dN), pyroglutamate (pQ), citrulline (Cit), L-asparagine (N), or glycine (G),
$[W]^2$ is tryptophan or D-tryptophan (dW),
$[T]^3$ is threonine, alanine (A), or lysine (K),
$[P]^4$ is proline, leucine (L), glutamate (E), arginine (R), D-alanine (dA), or D-valine (dV),
$[N]^5$ is asparagine or glutamine (Q),
$[A]^6$ is alanine, D-alanine (dA) or serine (S),
$[A]^7$ is alanine or methionine (M),
$[L]^8$ is leucine or glutamine (Q),
$[Y]^9$ is tyrosine,
$[L]^{10}$ is leucine,
$[F]^{11}$ is phenylalanine or leucine (L),
$[G]^{12}$ is glycine or D-alanine,
$[P]^{13}$ is proline or alanine (A),
$[Q]^{14}$ is glutamine, D-glutamine (dQ), or histidine (H), and
wherein the GALR2 agonist specifically activates galanin receptor type 2.

2. The GALR2 agonist according to claim 1, wherein the agonist has any one of the amino acid sequences set forth in formulas 2 to 4:

(2)

(3)

(4)

3. The GALR2 agonist according to claim 1, wherein the agonist does not activate galanin receptor type 1 (GALR1) and/or galanin receptor type 3 (GALR3).

4. The GALR2 agonist according to claim 1, wherein $[A]^{1'}$ is A and $[F]^{11}$ is F.

5. The GALR2 agonist according to claim 1, wherein $[N]^5$ is N, $[A]^7$ is A, and $[F]^{11}$ is F.

6. The GALR2 agonist according to claim 1, wherein $[N]^5$ is N, $[A]^7$ is A, $[F]^{11}$ is F, and $[P]^{13}$ is P.

7. The GALR2 agonist according to claim 1, wherein the first amino acid in the amino acid sequence is D-asparagine (dN).

8. The GALR2 agonist according to claim 1, wherein $[P]^4$ is dA or R.

9. The GALR2 agonist according to claim 1, wherein $[dN]^1$ is replaced with N, and wherein the N is protected with a polyethylene glycol (PEG), acetyl (Ac) group, or Fmoc.

10. A pharmaceutical composition comprising the GALR2 agonist according to claim 1 and a pharmaceutically acceptable carrier.

11. A pharmaceutical composition comprising the GALR2 agonist according to claim 4 and a pharmaceutically acceptable carrier.

12. A pharmaceutical composition comprising the GALR2 agonist according to claim 5 and a pharmaceutically acceptable carrier.

13. A pharmaceutical composition comprising the GALR2 agonist according to claim 6 and a pharmaceutically acceptable carrier.

14. A pharmaceutical composition comprising the GALR2 agonist according to claim 8 and a pharmaceutically acceptable carrier.

15. A peptide-based galanin receptor type 2 (GALR2) agonist comprising the amino acid sequence as set forth in SEQ ID NO: 9, SEQ ID NO: 12, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 31, SEQ ID NO: 32, SEQ ID NO: 33, SEQ ID NO: 37, SEQ ID NO: 39, SEQ ID NO: 40, SEQ ID NO: 41, SEQ ID NO: 44, SEQ ID NO: 45, SEQ ID NO: 47, SEQ ID NO: 51; SEQ ID NO: 52, SEQ ID NO: 53, SEQ ID NO: 54, SEQ ID NO: 55, SEQ ID NO: 56, SEQ ID NO: 57, SEQ ID NO: 58, or SEQ ID NO: 59, wherein the GALR2 agonist specifically activates galanin receptor type 2.

16. The GALR2 agonist according to claim 15, comprising the amino acid sequence as set forth in SEQ ID NO: 53, SEQ ID NO: 55, SEQ ID NO: 56, SEQ ID NO: 57, SEQ ID NO: 58, or SEQ ID NO: 59.

17. The GALR2 agonist according to claim 15, wherein the amino acid sequence is attached to polyethylene glycol (PEG), an acetyl (Ac) group, or Fmoc.

18. The GALR2 agonist according to claim 15, wherein the amino acid sequence is attached to $NH_2$ on the C-terminus.

19. A pharmaceutical composition comprising the GALR2 agonist according to claim 15 and a pharmaceutically acceptable carrier.

20. A pharmaceutical composition comprising the GALR2 agonist according to claim 16 and a pharmaceutically acceptable carrier.

* * * * *

SEQUENCE LISTING

```
<160> NUMBER OF SEQ ID NOS: 59

<210> SEQ ID NO 1
<211> LENGTH: 14
<212> TYPE: PRT
<213> ORGANISM: Artificial  Sequence
<220> FEATURE:
<223> OTHER INFORMATION: GALR2 agonists
<220> FEATURE:
<221> NAME/KEY: VARIANT
<222> LOCATION: (1)
<223> OTHER INFORMATION: 1st Asn is d-Asn
<220> FEATURE:
<221> NAME/KEY: VARIANT
<222> LOCATION: (2)
<223> OTHER INFORMATION: 2nd Trp may be substitutued with d-Trp or
      2-naphtyl
<220> FEATURE:
<221> NAME/KEY: VARIANT
<222> LOCATION: (3)
<223> OTHER INFORMATION: 3rd Thr may be substitutued with Ala or Lys
<220> FEATURE:
<221> NAME/KEY: VARIANT
<222> LOCATION: (4)
<223> OTHER INFORMATION: 4th Pro may be substitutued with d-Ala or d-Val
<220> FEATURE:
<221> NAME/KEY: VARIANT
<222> LOCATION: (5)
<223> OTHER INFORMATION: 5th Asn may be substitutued with Gln
<220> FEATURE:
<221> NAME/KEY: VARIANT
<222> LOCATION: (6)
<223> OTHER INFORMATION: 6th Ala may be substitutued with d-Ala
<220> FEATURE:
<221> NAME/KEY: VARIANT
<222> LOCATION: (7)
<223> OTHER INFORMATION: 7th Ala may be substitutued with Met
<220> FEATURE:
<221> NAME/KEY: VARIANT
<222> LOCATION: (11)
<223> OTHER INFORMATION: 11th Phe may be substitutued with Lys or Leu or
      Tyr
<220> FEATURE:
<221> NAME/KEY: VARIANT
<222> LOCATION: (13)
<223> OTHER INFORMATION: 13th Pro may be substitutued with d-Ala or Ala
<220> FEATURE:
<221> NAME/KEY: VARIANT
<222> LOCATION: (14)
<223> OTHER INFORMATION: 14th Gln may be substitutued with d-Gln or His

<400> SEQUENCE: 1

Asn Trp Thr Pro Asn Ala Ala Leu Tyr Leu Phe Gly Pro Gln
1               5                   10

<210> SEQ ID NO 2
<211> LENGTH: 14
<212> TYPE: PRT
<213> ORGANISM: Artificial Sequence
<220> FEATURE:
<223> OTHER INFORMATION: GALR2 agonist
<220> FEATURE:
```

```
<221> NAME/KEY: VARIANT
<222> LOCATION: (1)..(14)
<223> OTHER INFORMATION: 1st Asn is d-Asn

<400> SEQUENCE: 2

Asn Trp Thr Pro Asn Ala Ala Leu Tyr Leu Phe Gly Pro Gln
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Hu_GAL

<400> SEQUENCE: 3

Gly Trp Thr Leu Asn Ser Ala Gly Tyr Leu Leu Gly Pro His
1               5                   10

<210> SEQ ID NO 4
<211> LENGTH: 14
<212> TYPE: PRT
<213> ORGANISM: Artificial Sequence
<220> FEATURE:
<223> OTHER INFORMATION: HU_GALP

<400> SEQUENCE: 4

Gly Trp Thr Leu Asn Ser Ala Gly Tyr Leu Leu Gly Pro Val
1               5                   10

<210> SEQ ID NO 5
<211> LENGTH: 14
<212> TYPE: PRT
<213> ORGANISM: Artificial Sequence
<220> FEATURE:
<223> OTHER INFORMATION: CO_SPX2

<400> SEQUENCE: 5

Asn Trp Gly Pro Gln Ser Met Leu Tyr Leu Lys Gly Arg Tyr
1               5                   10

<210> SEQ ID NO 6
<211> LENGTH: 14
<212> TYPE: PRT
<213> ORGANISM: Artificial Sequence
<220> FEATURE:
<223> OTHER INFORMATION: HU_SPX1

<400> SEQUENCE: 6

Asn Trp Thr Pro Gln Ala Met Leu Tyr Leu Lys Gly Ala Gln
1               5                   10

<210> SEQ ID NO 7

<400> SEQUENCE: 7

000

<210> SEQ ID NO 8
<211> LENGTH: 14
<212> TYPE: PRT
<213> ORGANISM: Artificial Sequence
<220> FEATURE:
<223> OTHER INFORMATION: h/m SPX

<400> SEQUENCE: 8

Asn Trp Thr Pro Gln Ala Met Leu Tyr Leu Lys Gly Ala Gln
```

<210> SEQ ID NO 9
<211> LENGTH: 14
<212> TYPE: PRT
<213> ORGANISM: Artificial Sequence
<220> FEATURE:
<223> OTHER INFORMATION: [dN1]-SPX
<220> FEATURE:
<221> NAME/KEY: misc_feature
<222> LOCATION: (1)..(1)
<223> OTHER INFORMATION: Asn is substituted with d-Asn

<400> SEQUENCE: 9

Asn Trp Thr Pro Gln Ala Met Leu Tyr Leu Lys Gly Ala Gln
1               5                   10

<210> SEQ ID NO 10
<211> LENGTH: 14
<212> TYPE: PRT
<213> ORGANISM: Artificial Sequence
<220> FEATURE:
<223> OTHER INFORMATION: [pQ1]-SPX
<220> FEATURE:
<221> NAME/KEY: MISC_FEATURE
<222> LOCATION: (1)..(1)
<223> OTHER INFORMATION: Asn is replaced with pyroglutamate

<400> SEQUENCE: 10

Asn Trp Thr Pro Gln Ala Met Leu Tyr Leu Lys Gly Ala Gln
1               5                   10

<210> SEQ ID NO 11
<211> LENGTH: 14
<212> TYPE: PRT
<213> ORGANISM: Artificial Sequence
<220> FEATURE:
<223> OTHER INFORMATION: [Ac-N1]-SPX
<220> FEATURE:
<221> NAME/KEY: MISC_FEATURE
<222> LOCATION: (1)..(1)
<223> OTHER INFORMATION: Asn is replaced by Asn protected by Acetyl (Ac)
      group

<400> SEQUENCE: 11

Asn Trp Thr Pro Gln Ala Met Leu Tyr Leu Lys Gly Ala Gln
1               5                   10

<210> SEQ ID NO 12
<211> LENGTH: 14
<212> TYPE: PRT
<213> ORGANISM: Artificial Sequence
<220> FEATURE:
<223> OTHER INFORMATION: [G1]-SPX

<400> SEQUENCE: 12

Gly Trp Thr Pro Gln Ala Met Leu Tyr Leu Lys Gly Ala Gln
1               5                   10

<210> SEQ ID NO 13
<211> LENGTH: 14
<212> TYPE: PRT
<213> ORGANISM: Artificial Sequence
<220> FEATURE:
<223> OTHER INFORMATION: [dW2]-SPX
<220> FEATURE:
<221> NAME/KEY: misc_feature
<222> LOCATION: (2)..(2)
<223> OTHER INFORMATION: Trp is replaced with with d-Trp

```
<400> SEQUENCE: 13

Asn Trp Thr Pro Gln Ala Met Leu Tyr Leu Lys Gly Ala Gln
1               5                   10

<210> SEQ ID NO 14
<211> LENGTH: 14
<212> TYPE: PRT
<213> ORGANISM: Artificial Sequence
<220> FEATURE:
<223> OTHER INFORMATION: [2Nal2]-SPX
<220> FEATURE:
<221> NAME/KEY: misc_feature
<222> LOCATION: (2)..(2)
<223> OTHER INFORMATION: Trp is replaced with 2-Naphytl group

<400> SEQUENCE: 14

Asn Trp Thr Pro Gln Ala Met Leu Tyr Leu Lys Gly Ala Gln
1               5                   10

<210> SEQ ID NO 15
<211> LENGTH: 14
<212> TYPE: PRT
<213> ORGANISM: Artificial Sequence
<220> FEATURE:
<223> OTHER INFORMATION: [dT3]-SPX
<220> FEATURE:
<221> NAME/KEY: MISC_FEATURE
<222> LOCATION: (3)..(3)
<223> OTHER INFORMATION: Thr is replaced by d-Thr

<400> SEQUENCE: 15

Asn Trp Thr Pro Gln Ala Met Leu Tyr Leu Lys Gly Ala Gln
1               5                   10

<210> SEQ ID NO 16
<211> LENGTH: 14
<212> TYPE: PRT
<213> ORGANISM: Artificial Sequence
<220> FEATURE:
<223> OTHER INFORMATION: [A3]-SPX

<400> SEQUENCE: 16

Asn Trp Ala Pro Gln Ala Met Leu Tyr Leu Lys Gly Ala Gln
1               5                   10

<210> SEQ ID NO 17
<211> LENGTH: 14
<212> TYPE: PRT
<213> ORGANISM: Artificial Sequence
<220> FEATURE:
<223> OTHER INFORMATION: [K3]-SPX

<400> SEQUENCE: 17

Asn Trp Lys Pro Gln Ala Met Leu Tyr Leu Lys Gly Ala Gln
1               5                   10

<210> SEQ ID NO 18
<211> LENGTH: 14
<212> TYPE: PRT
<213> ORGANISM: Artificial Sequence
<220> FEATURE:
<223> OTHER INFORMATION: [dA4]-SPX
<220> FEATURE:
<221> NAME/KEY: MISC_FEATURE
<222> LOCATION: (4)..(4)
<223> OTHER INFORMATION: Ala is replaced by d-Ala

<400> SEQUENCE: 18
```

Asn Trp Thr Ala Gln Ala Met Leu Tyr Leu Lys Gly Ala Gln
1               5                   10

<210> SEQ ID NO 19
<211> LENGTH: 14
<212> TYPE: PRT
<213> ORGANISM: Artificial Sequence
<220> FEATURE:
<223> OTHER INFORMATION: [E4]-SPX

<400> SEQUENCE: 19

Asn Trp Thr Glu Gln Ala Met Leu Tyr Leu Lys Gly Ala Gln
1               5                   10

<210> SEQ ID NO 20
<211> LENGTH: 14
<212> TYPE: PRT
<213> ORGANISM: Artificial Sequence
<220> FEATURE:
<223> OTHER INFORMATION: [L4]-SPX

<400> SEQUENCE: 20

Asn Trp Thr Leu Gln Ala Met Leu Tyr Leu Lys Gly Ala Gln
1               5                   10

<210> SEQ ID NO 21
<211> LENGTH: 14
<212> TYPE: PRT
<213> ORGANISM: Artificial Sequence
<220> FEATURE:
<223> OTHER INFORMATION: [R4]-SPX

<400> SEQUENCE: 21

Asn Trp Thr Arg Gln Ala Met Leu Tyr Leu Lys Gly Ala Gln
1               5                   10

<210> SEQ ID NO 22
<211> LENGTH: 14
<212> TYPE: PRT
<213> ORGANISM: Artificial Sequence
<220> FEATURE:
<223> OTHER INFORMATION: [dV4]-SPX
<220> FEATURE:
<221> NAME/KEY: MISC_FEATURE
<222> LOCATION: (4)..(4)
<223> OTHER INFORMATION: Val is replaced with d-Val

<400> SEQUENCE: 22

Asn Trp Thr Val Gln Ala Met Leu Tyr Leu Lys Gly Ala Gln
1               5                   10

<210> SEQ ID NO 23
<211> LENGTH: 14
<212> TYPE: PRT
<213> ORGANISM: Artificial Sequence
<220> FEATURE:
<223> OTHER INFORMATION: [N5]-SPX

<400> SEQUENCE: 23

Asn Trp Thr Pro Asn Ala Met Leu Tyr Leu Lys Gly Ala Gln
1               5                   10

<210> SEQ ID NO 24
<211> LENGTH: 14
<212> TYPE: PRT
<213> ORGANISM: Artificial Sequence
<220> FEATURE:
<223> OTHER INFORMATION: [dA6]-SPX

```
<220> FEATURE:
<221> NAME/KEY: misc_feature
<222> LOCATION: (6)..(6)
<223> OTHER INFORMATION: Ala is replaced with d-Ala

<400> SEQUENCE: 24

Asn Trp Thr Pro Gln Ala Met Leu Tyr Leu Lys Gly Ala Gln
 1               5                  10

<210> SEQ ID NO 25
<211> LENGTH: 14
<212> TYPE: PRT
<213> ORGANISM: Artificial Sequence
<220> FEATURE:
<223> OTHER INFORMATION: [A7]-SPX

<400> SEQUENCE: 25

Asn Trp Thr Pro Gln Ala Ala Leu Tyr Leu Lys Gly Ala Gln
 1               5                  10

<210> SEQ ID NO 26
<211> LENGTH: 14
<212> TYPE: PRT
<213> ORGANISM: Artificial Sequence
<220> FEATURE:
<223> OTHER INFORMATION: [G8]-SPX

<400> SEQUENCE: 26

Asn Trp Thr Pro Gln Ala Met Gly Tyr Leu Lys Gly Ala Gln
 1               5                  10

<210> SEQ ID NO 27
<211> LENGTH: 14
<212> TYPE: PRT
<213> ORGANISM: Artificial Sequence
<220> FEATURE:
<223> OTHER INFORMATION: [Q8]-SPX

<400> SEQUENCE: 27

Asn Trp Thr Pro Gln Ala Met Gln Tyr Leu Lys Gly Ala Gln
 1               5                  10

<210> SEQ ID NO 28
<211> LENGTH: 14
<212> TYPE: PRT
<213> ORGANISM: Artificial Sequence
<220> FEATURE:
<223> OTHER INFORMATION: [F9]-SPX

<400> SEQUENCE: 28

Asn Trp Thr Pro Gln Ala Met Leu Phe Leu Lys Gly Ala Gln
 1               5                  10

<210> SEQ ID NO 29
<211> LENGTH: 14
<212> TYPE: PRT
<213> ORGANISM: Artificial Sequence
<220> FEATURE:
<223> OTHER INFORMATION: [dY9]-SPX
<220> FEATURE:
<221> NAME/KEY: misc_feature
<222> LOCATION: (9)..(9)
<223> OTHER INFORMATION: Tyr is replaced with d-Tyr

<400> SEQUENCE: 29

Asn Trp Thr Pro Gln Ala Met Leu Tyr Leu Lys Gly Ala Gln
 1               5                  10
```

<210> SEQ ID NO 30
<211> LENGTH: 14
<212> TYPE: PRT
<213> ORGANISM: Artificial Sequence
<220> FEATURE:
<223> OTHER INFORMATION: [dL10]-SPX
<220> FEATURE:
<221> NAME/KEY: misc_feature
<222> LOCATION: (10)..(10)
<223> OTHER INFORMATION: Leu is replaced with d-Leu

<400> SEQUENCE: 30

Asn Trp Thr Pro Gln Ala Met Leu Tyr Leu Lys Gly Ala Gln
1               5                   10

<210> SEQ ID NO 31
<211> LENGTH: 14
<212> TYPE: PRT
<213> ORGANISM: Artificial Sequence
<220> FEATURE:
<223> OTHER INFORMATION: [F11]-SPX

<400> SEQUENCE: 31

Asn Trp Thr Pro Gln Ala Met Leu Tyr Leu Phe Gly Ala Gln
1               5                   10

<210> SEQ ID NO 32
<211> LENGTH: 14
<212> TYPE: PRT
<213> ORGANISM: Artificial Sequence
<220> FEATURE:
<223> OTHER INFORMATION: [L11]-SPX

<400> SEQUENCE: 32

Asn Trp Thr Pro Gln Ala Met Leu Tyr Leu Leu Gly Ala Gln
1               5                   10

<210> SEQ ID NO 33
<211> LENGTH: 14
<212> TYPE: PRT
<213> ORGANISM: Artificial Sequence
<220> FEATURE:
<223> OTHER INFORMATION: [Y11]-SPX

<400> SEQUENCE: 33

Asn Trp Thr Pro Gln Ala Met Leu Tyr Leu Tyr Gly Ala Gln
1               5                   10

<210> SEQ ID NO 34
<211> LENGTH: 14
<212> TYPE: PRT
<213> ORGANISM: Artificial Sequence
<220> FEATURE:
<223> OTHER INFORMATION: [dK11]-SPX
<220> FEATURE:
<221> NAME/KEY: misc_feature
<222> LOCATION: (11)..(11)
<223> OTHER INFORMATION: Lys is replaced with d-Lys

<400> SEQUENCE: 34

Asn Trp Thr Pro Gln Ala Met Leu Tyr Leu Lys Gly Ala Gln
1               5                   10

<210> SEQ ID NO 35
<211> LENGTH: 11
<212> TYPE: PRT
<213> ORGANISM: Artificial Sequence
<220> FEATURE:

<223> OTHER INFORMATION: k Synthetic SPX

<400> SEQUENCE: 35

Asn Trp Thr Pro Gln Ala Met Leu Tyr Leu Lys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: [D11]-SPX

<400> SEQUENCE: 36

Asn Trp Thr Pro Gln Ala Met Leu Tyr Leu Asp Gly Ala Gln
1               5                   10

<210> SEQ ID NO 37
<211> LENGTH: 14
<212> TYPE: PRT
<213> ORGANISM: Artificial Sequence
<220> FEATURE:
<223> OTHER INFORMATION: [dA12]-SPX
<220> FEATURE:
<221> NAME/KEY: misc_feature
<222> LOCATION: (12)..(12)
<223> OTHER INFORMATION: Ala is replaced with d-Ala

<400> SEQUENCE: 37

Asn Trp Thr Pro Gln Ala Met Leu Tyr Leu Lys Ala Ala Gln
1               5                   10

<210> SEQ ID NO 38
<211> LENGTH: 14
<212> TYPE: PRT
<213> ORGANISM: Artificial Sequence
<220> FEATURE:
<223> OTHER INFORMATION: [dA13]-SPX
<220> FEATURE:
<221> NAME/KEY: misc_feature
<222> LOCATION: (13)..(13)
<223> OTHER INFORMATION: Ala is replaced with d-Ala

<400> SEQUENCE: 38

Asn Trp Thr Pro Gln Ala Met Leu Tyr Leu Lys Gly Ala Gln
1               5                   10

<210> SEQ ID NO 39
<211> LENGTH: 14
<212> TYPE: PRT
<213> ORGANISM: Artificial Sequence
<220> FEATURE:
<223> OTHER INFORMATION: [P13]-SPX

<400> SEQUENCE: 39

Asn Trp Thr Pro Gln Ala Met Leu Tyr Leu Lys Gly Pro Gln
1               5                   10

<210> SEQ ID NO 40
<211> LENGTH: 14
<212> TYPE: PRT
<213> ORGANISM: Artificial Sequence
<220> FEATURE:
<223> OTHER INFORMATION: [dQ14]-SPX
<220> FEATURE:
<221> NAME/KEY: misc_feature
<222> LOCATION: (14)..(14)
<223> OTHER INFORMATION: Gln is replaced with d-Gln

```
<400> SEQUENCE: 40

Asn Trp Thr Pro Gln Ala Met Leu Tyr Leu Lys Gly Ala Gln
1               5                   10

<210> SEQ ID NO 41
<211> LENGTH: 14
<212> TYPE: PRT
<213> ORGANISM: Artificial Sequence
<220> FEATURE:
<223> OTHER INFORMATION: [H14]-SPX

<400> SEQUENCE: 41

Asn Trp Thr Pro Gln Ala Met Leu Tyr Leu Lys Gly Ala His
1               5                   10

<210> SEQ ID NO 42
<211> LENGTH: 14
<212> TYPE: PRT
<213> ORGANISM: Artificial Sequence
<220> FEATURE:
<223> OTHER INFORMATION: [PEG]-SPX
<220> FEATURE:
<221> NAME/KEY: MISC_FEATURE
<222> LOCATION: (1)..(1)
<223> OTHER INFORMATION: Asn is modified with polyethylene glycol (PEG)

<400> SEQUENCE: 42

Asn Trp Thr Pro Gln Ala Met Leu Tyr Leu Lys Gly Ala Gln
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Cyclic-SPX
<220> FEATURE:
<221> NAME/KEY: MISC_FEATURE
<222> LOCATION: (1)..(1)
<223> OTHER INFORMATION: Asn is Cyclo modified

<400> SEQUENCE: 43

Asn Trp Thr Pro Gln Ala Met Leu Tyr Leu Lys Gly Ala Gln
1               5                   10

<210> SEQ ID NO 44
<211> LENGTH: 14
<212> TYPE: PRT
<213> ORGANISM: Artificial Sequence
<220> FEATURE:
<223> OTHER INFORMATION: [Cit1]-SPX
<220> FEATURE:
<221> NAME/KEY: misc_feature
<222> LOCATION: (1)..(1)
<223> OTHER INFORMATION: Asn is replaced with a Citrulline

<400> SEQUENCE: 44

Asn Trp Thr Pro Gln Ala Met Leu Tyr Leu Lys Gly Ala Gln
1               5                   10

<210> SEQ ID NO 45
<211> LENGTH: 14
<212> TYPE: PRT
<213> ORGANISM: Artificial Sequence
<220> FEATURE:
<223> OTHER INFORMATION: [Fmoc]-SPX
<220> FEATURE:
<221> NAME/KEY: misc_feature
<222> LOCATION: (1)..(1)
```

<223> OTHER INFORMATION: Asn is replaced with Fmoc group

<400> SEQUENCE: 45

Asn Trp Thr Pro Gln Ala Met Leu Tyr Leu Lys Gly Ala Gln
1               5                   10

<210> SEQ ID NO 46
<211> LENGTH: 14
<212> TYPE: PRT
<213> ORGANISM: Artificial Sequence
<220> FEATURE:
<223> OTHER INFORMATION: [Fmoc-dT3]-SPX
<220> FEATURE:
<221> NAME/KEY: misc_feature
<222> LOCATION: (1)..(1)
<223> OTHER INFORMATION: Asn is replaced with Fmoc group
<220> FEATURE:
<221> NAME/KEY: misc_feature
<222> LOCATION: (3)..(3)
<223> OTHER INFORMATION: Thr is replaced with d-Thr

<400> SEQUENCE: 46

Asn Trp Thr Pro Gln Ala Met Leu Tyr Leu Lys Gly Ala Gln
1               5                   10

<210> SEQ ID NO 47
<211> LENGTH: 20
<212> TYPE: PRT
<213> ORGANISM: Artificial Sequence
<220> FEATURE:
<223> OTHER INFORMATION: SPX-m40

<400> SEQUENCE: 47

Asn Trp Thr Pro Gln Ala Met Leu Tyr Leu Lys Gly Ala Pro Pro Ala
1               5                   10                  15

Leu Ala Leu Ala
            20

<210> SEQ ID NO 48
<211> LENGTH: 14
<212> TYPE: PRT
<213> ORGANISM: Artificial Sequence
<220> FEATURE:
<223> OTHER INFORMATION: [A7][F11]-SPX

<400> SEQUENCE: 48

Asn Trp Thr Pro Gln Ala Ala Leu Tyr Leu Phe Gly Ala Gln
1               5                   10

<210> SEQ ID NO 49
<211> LENGTH: 12
<212> TYPE: PRT
<213> ORGANISM: Artificial Sequence
<220> FEATURE:
<223> OTHER INFORMATION: [R11][F12]-SPX

<400> SEQUENCE: 49

Asn Trp Thr Pro Gln Ala Met Leu Tyr Leu Arg Phe
1               5                   10

<210> SEQ ID NO 50
<211> LENGTH: 14
<212> TYPE: PRT
<213> ORGANISM: Artificial Sequence
<220> FEATURE:
<223> OTHER INFORMATION: [N5][A7][F11]-SPX

<400> SEQUENCE: 50

Asn Trp Thr Pro Asn Ala Ala Leu Tyr Leu Phe Gly Ala Gln
1               5                   10

<210> SEQ ID NO 51
<211> LENGTH: 14
<212> TYPE: PRT
<213> ORGANISM: Artificial Sequence
<220> FEATURE:
<223> OTHER INFORMATION: [N5][A7][F11][P13]-SPX

<400> SEQUENCE: 51

Asn Trp Thr Pro Asn Ala Ala Leu Tyr Leu Phe Gly Pro Gln
1               5                   10

<210> SEQ ID NO 52
<211> LENGTH: 14
<212> TYPE: PRT
<213> ORGANISM: Artificial Sequence
<220> FEATURE:
<223> OTHER INFORMATION: [N5][A7][F11][H14]-SPX

<400> SEQUENCE: 52

Asn Trp Thr Pro Asn Ala Ala Leu Tyr Leu Phe Gly Ala His
1               5                   10

<210> SEQ ID NO 53
<211> LENGTH: 14
<212> TYPE: PRT
<213> ORGANISM: Artificial Sequence
<220> FEATURE:
<223> OTHER INFORMATION: PEG2-SPX

<400> SEQUENCE: 53

Asn Trp Thr Pro Asn Ala Ala Leu Tyr Leu Phe Gly Ala His
1               5                   10

<210> SEQ ID NO 54
<211> LENGTH: 14
<212> TYPE: PRT
<213> ORGANISM: Artificial Sequence
<220> FEATURE:
<223> OTHER INFORMATION: [3-NO2_Y9]-SPX
<220> FEATURE:
<221> NAME/KEY: misc_feature
<222> LOCATION: (9)..(9)
<223> OTHER INFORMATION: Y is replaced with NO2I

<400> SEQUENCE: 54

Asn Trp Thr Pro Gln Ala Met Leu Tyr Leu Lys Gly Ala Gln
1               5                   10

<210> SEQ ID NO 55
<211> LENGTH: 14
<212> TYPE: PRT
<213> ORGANISM: Artificial Sequence
<220> FEATURE:
<223> OTHER INFORMATION: [Fmoc-Qu]-SPX
<220> FEATURE:
<221> NAME/KEY: misc_feature
<222> LOCATION: (1)..(1)
<223> OTHER INFORMATION: Asn is modified with Fmoc group

<400> SEQUENCE: 55

Asn Trp Thr Pro Asn Ala Ala Leu Tyr Leu Phe Gly Pro Gln
1               5                   10

<210> SEQ ID NO 56

-continued

```
<211> LENGTH: 14
<212> TYPE: PRT
<213> ORGANISM: Artificial Sequence
<220> FEATURE:
<223> OTHER INFORMATION: [Fmoc-Qu-dQ14]-SPX
<220> FEATURE:
<221> NAME/KEY: misc_feature
<222> LOCATION: (1)..(1)
<223> OTHER INFORMATION: Asn is modified with Fmoc group
<220> FEATURE:
<221> NAME/KEY: misc_feature
<222> LOCATION: (14)..(14)
<223> OTHER INFORMATION: Gln is replaced with d-Gln

<400> SEQUENCE: 56

Asn Trp Thr Pro Asn Ala Ala Leu Tyr Leu Phe Gly Pro Gln
1               5                   10

<210> SEQ ID NO 57
<211> LENGTH: 14
<212> TYPE: PRT
<213> ORGANISM: Artificial Sequence
<220> FEATURE:
<223> OTHER INFORMATION: [Fmoc-Qu-dA4]-SPX
<220> FEATURE:
<221> NAME/KEY: misc_feature
<222> LOCATION: (1)..(1)
<223> OTHER INFORMATION: Asn is modified with Fmoc Group
<220> FEATURE:
<221> NAME/KEY: misc_feature
<222> LOCATION: (4)..(4)
<223> OTHER INFORMATION: Ala is replaced with d-Ala

<400> SEQUENCE: 57

Asn Trp Thr Ala Asn Ala Ala Leu Tyr Leu Phe Gly Pro Gln
1               5                   10

<210> SEQ ID NO 58
<211> LENGTH: 14
<212> TYPE: PRT
<213> ORGANISM: Artificial Sequence
<220> FEATURE:
<223> OTHER INFORMATION: [Fmoc-Qu-dA4-dQ14]-SPX
<220> FEATURE:
<221> NAME/KEY: misc_feature
<222> LOCATION: (1)..(1)
<223> OTHER INFORMATION: Asn is modified with Fmoc Group
<220> FEATURE:
<221> NAME/KEY: misc_feature
<222> LOCATION: (4)..(4)
<223> OTHER INFORMATION: Ala is replaced with d-Ala
<220> FEATURE:
<221> NAME/KEY: misc_feature
<222> LOCATION: (14)..(14)
<223> OTHER INFORMATION: Gln is replaced with d-Gln

<400> SEQUENCE: 58

Asn Trp Thr Ala Asn Ala Ala Leu Tyr Leu Phe Gly Pro Gln
1               5                   10

<210> SEQ ID NO 59
<211> LENGTH: 14
<212> TYPE: PRT
<213> ORGANISM: Artificial Sequence
<220> FEATURE:
<223> OTHER INFORMATION: [PEG-Qu-dA4-dQ14]-SPX
<220> FEATURE:
<221> NAME/KEY: misc_feature
<222> LOCATION: (1)..(1)
<223> OTHER INFORMATION: Asn is modified with Polyethylene Glycol (PEG)
<220> FEATURE:
<221> NAME/KEY: misc_feature
<222> LOCATION: (4)..(4)
```

```
<223> OTHER INFORMATION: Ala is replaced with d-Ala
<220> FEATURE:
<221> NAME/KEY: misc_feature
<222> LOCATION: (14)..(14)
<223> OTHER INFORMATION: Gln is replaced with d-Gln

<400> SEQUENCE: 59

Asn Trp Thr Ala Asn Ala Ala Leu Tyr Leu Phe Gly Pro Gln
1               5                   10
```